United States Patent
Moraes et al.

(10) Patent No.: US 8,557,582 B2
(45) Date of Patent: Oct. 15, 2013

(54) SYSTEM, APPARATUS AND METHOD FOR APPLYING MECHANICAL FORCE TO A MATERIAL

(76) Inventors: Christopher Moraes, Scarborough (CA); Craig Simmons, Toronto (CA); Yu Sun, Toronto (CA)

(*) Notice: Subject to any disclaimer, the term of this patent is extended or adjusted under 35 U.S.C. 154(b) by 915 days.

(21) Appl. No.: 12/240,310

(22) Filed: Sep. 29, 2008

(65) Prior Publication Data
US 2009/0088342 A1 Apr. 2, 2009

Related U.S. Application Data

(60) Provisional application No. 60/976,069, filed on Sep. 28, 2007.

(51) Int. Cl.
 C12M 3/00 (2006.01)
 C12M 1/22 (2006.01)
 C12N 5/00 (2006.01)

(52) U.S. Cl.
 USPC ............. 435/401; 435/288.3; 435/288.4; 435/289.1; 435/305.1; 435/305.2; 435/305.3; 435/375

(58) Field of Classification Search
 USPC .......... 435/289.1, 288.3, 288.4, 305.1, 305.2, 435/305.4, 305.3, 375, 401
 See application file for complete search history.

(56) References Cited

U.S. PATENT DOCUMENTS

| | | | |
|---|---|---|---|
| 4,839,280 A * | 6/1989 | Banes | 435/305.2 |
| 5,348,879 A * | 9/1994 | Shapiro et al. | 435/375 |
| 5,553,486 A | 9/1996 | Bonin | |
| 5,672,830 A | 9/1997 | Rogers et al. | |
| 6,037,141 A | 3/2000 | Banes | |
| 6,048,723 A | 4/2000 | Banes | |
| 6,218,178 B1 | 4/2001 | Banes | |
| 6,645,759 B2 * | 11/2003 | Banes | 435/293.1 |
| 6,772,642 B2 | 8/2004 | Hajduk et al. | |
| 6,793,753 B2 | 9/2004 | Unger et al. | |
| 2007/0234785 A1 * | 10/2007 | Beerling et al. | 73/61.56 |

OTHER PUBLICATIONS

Wang, J. and Thampatty, B.P., An Introductory Review of Cell Mechanobiology, Biomechanics and Modeling in Mechanobiology, 2006, 1-16, vol. 5-1, Springer Berlin/Heidelberg.

Unger, Marc A., et. al., Monolithic Microfabricated Valves and Pumps by Multilayer Soft Lithography, 2000, Science, 113-116, vol. 288, American Assoc. for the Advancement of . . . .

McBeath, Rowena, et. al., Cell Shape, Cytoskeletal Tension, and RhoA Regute Stem Cell Lineage Commitment, Development Cell, 2004, 483-495, vol. 6, Cell Press,USA.

Liu, Valerie A., et. al., Three-Dimensional Photopatterning of Hydrogels Containing Living Cells, Biomedical Microdevices, 2002, 257-266, vol. 4:4, Kluwer Academic Publishers.

(Continued)

*Primary Examiner* — Nathan Bowers
*Assistant Examiner* — Gautam Prakash
(74) *Attorney, Agent, or Firm* — Miller Thomson LLP; Eduardo Krupnik

(57) ABSTRACT

The present invention details the design and operation of a miniaturized device array in which a range of simultaneous mechanical forces are produced by a single external pressure source. The invention is primarily embodied in a microfabricated device arrays designed to rapidly probe biological cell response to various combinations of mechanical, chemical and extra-cellular matrix parameters in a high-throughput fashion.

26 Claims, 25 Drawing Sheets

(56) References Cited

OTHER PUBLICATIONS

Kane, Ravi S., et. al., Patterning Proteins and Cells Using Soft Lithography, Biomaterials, 1999, 2363,2376, vol. 20, Elsevier Science Ltd.

Jo, Byung-Ho, et. al., Three-Dimensional Micro-Channel Fabrication in Polydimethylsiloxane (PDMS) Elastomer, Journal of Microelectromechanical Systmes, 2000, 76-81, vol. 9-1.

* cited by examiner

Pressure Distribution Channel Schematic #1

Pressure Distribution Channel Schematic #2

SYSTEM, APPARATUS AND METHOD FOR APPLYING MECHANICAL FORCE TO A MATERIAL

PRIORITY INFORMATION

This application claims priority from U.S. Provisional Patent Application No. 60/976,069 filed Sep. 28, 2007.

FIELD OF THE INVENTION

The present invention relates to the field of microsystems and devices. The present invention in particular relates to an apparatus comprising an array of devices for applying strain to a material and methods of using said apparatus. The present invention includes applications in the fields of biomedical engineering.

BACKGROUND OF THE INVENTION

High-throughput screening (HTS) is a method used in life science research and the biopharmaceutical industry for drug discovery, toxicology testing, and functional genomics. Typically, HTS is used to rapidly determine the physiological response of groups of cells to various combinations and quantities of biologically active chemical compounds and biomaterials surrounding the cell.

Cellular activity is also influenced by applied mechanical stimulation, which has been shown to have a strong impact on biological function in certain types of cells (McBeath, et al., Dev. Cell 2004; Wang & Thampatty, Biomech Model Mechanobiol 2006; Saha et al., J Cell Physiol, 2006). Existing experimental techniques are unable to adequately characterize cellular response to varying degrees of mechanical stimulation with a high accuracy in a high-throughput manner. These limitations have prevented systematic investigations into the effects of mechanical stimuli on cell behaviour and hindered discovery of new control strategies for cell-based therapies.

Furthermore, despite the demonstrated individual importance of mechanical forces; chemical cues; and the composition and structure of surrounding biomaterials in regulated cellular function, the lack of HTS techniques for mechanical factors precludes the ability to effectively study combinations of these various parameters. This patent application discloses a system designed to meet this need for rapidly probing either single cells or colonies of cells.

Existing low-throughput experimental techniques in this field make use of three main mechanical loading schemes to probe cellular response: compressive loading, deformation of the substrate to which cells adhere, and fluid flow-induced shear stresses. U.S. Pat. No. 6,048,723 discloses a flexible bottom culture plate for applying mechanical loads to cell culture; U.S. Pat. No. 6,218,178 discloses the loading assembly for the plates of U.S. Pat. No. 6,048,723; U.S. Pat. No. 6,645,759 discloses a device for growing cells in culture under shear stress and/or strain; and U.S. Pat. No. 6,037,141 discloses a system for culturing cells under compression conditions. However, the systems described the cited US patents are all low-throughput, applying a single strain across at most, six experimental locations. This drawback significantly impacts the time required to perform such studies. It also precludes the ability to perform combinatorial manipulation of chemical and mechanical parameters, as can be performed in our disclosed invention.

Moreover, there are two modes of cell culture: two-dimensional culture on a flat surface, and three-dimensional culture within a porous biomaterial. Each of these culture techniques and loading scenarios provide insight into the inner workings of the cell, but typically require radically different experimental setups.

Microsystems are engineered systems with critical structural or functional features of micrometers, where the microfabricated component of the system typically ranges in size from millimeters to centimeters. They have such advantages as low cost, small size, minimal reagent consumption and fast response time. Because of the reduced system footprint, a dense array of functional sub-units is possible, and as such they are ideal for developing array based HTS systems. Similarities between system feature sizes and the size of a cell make this technology suitable for developing HTS systems for single- or multi-cell biology. Advances in microfabrication have enabled the rapid development of complex, elastomeric, monolithic polymer structures with well-defined features with a resolution of micrometers. To provide an example, these techniques—termed Multilayer Soft Lithography (MSL)—have been used to develop a fully controllable microfluidic network, actuated by a number of 2-state valves (Unger et al., "Monolithic microfabricated valves and pumps by multilayer soft lithography," Science, vol. 288, pp. 113-6, Apr. 7 2000; and U.S. Pat. No. 6,793,753).

In view of the foregoing, an improved apparatus, system and method for HTS applications is desirable.

The disclosed invention introduces new aspects in MSL device development, including the use of mechanical solid elements in an all-polymer device, and the application of a single pressure load to obtain a range of mechanical activity.

SUMMARY OF THE INVENTION

The present invention relates to an apparatus for applying mechanical forces of varying magnitudes to a material and methods of using said apparatus.

In one aspect, the present invention is an apparatus for applying mechanical forces of varying magnitudes to a material characterized in that the apparatus comprises at least one array defining a surface and a plurality of actuation devices disposed thereon, each of said actuation devices having a structural configuration, said structural configuration including an opening; and a flexible membrane fixed to the surface and covering said opening, said membrane having an upper surface that permits attachment of the material thereto, wherein the array is structured to enable pressure or vacuum to be delivered to the plurality of actuation devices, and wherein the array is further structured to enable variation of said structural configuration from actuation device to actuation device such that the delivery of pressure or vacuum to the plurality of actuation devices results in application of varying magnitudes of mechanical force to the material by means of actuation of the flexible membrane covering said openings_based on the structural configuration thereof.

In one aspect the strain fields produced by the mechanical, forces on the material comprise non-uniform strain fields of varying magnitudes on the material.

In another aspect, the present invention is an apparatus for applying mechanical forces of varying magnitudes to a material comprising at least one array defining a surface and a plurality of actuation devices disposed thereon, each of said actuation devices having a structural configuration, said structural configuration including: (i) a base including a first opening, (ii) a flexible actuation membrane fixed to the base and covering said first opening, said actuation membrane having an upper surface; and (iii) an upper structure resting on said upper surface of the actuation membrane and including a second opening that opens on the surface; a moving member extending from the upper surface of the actuation membrane into the upper structure towards the second opening; a substrate membrane fixed to the surface and covering said second opening, said substrate membrane having an upper surface that permits attachment of the material thereto, wherein the array is structured to enable pressure or vacuum to be delivered to the plurality of actuation devices, and wherein the array is further structured to enable variation of said structural configuration from actuation device to actuation device such that the delivery of pressure or vacuum to the plurality of actuation devices results in application of varying magnitudes of mechanical force to the material by means of actuation of the actuation membrane covering said first openings based on the structural configuration thereof thereby moving said moving member to direct the mechanical force to the material.

In one aspect of the disclosed invention, the strain fields comprise various uniform strain fields of varying magnitudes on the material.

In yet another aspect of the invention is an apparatus for applying mechanical forces of varying magnitudes to a material characterized in that the apparatus comprises: at least one array defining a surface and a plurality of actuation devices disposed thereon, each of said actuation devices having a structural configuration, said structural configuration including an opening; a flexible membrane fixed to the surface and covering said opening, said membrane having an upper surface; a moving member extending from the upper side of the membrane and having a top that permits attachment of the material thereto; and a weight means, wherein the array is structured to enable pressure or vacuum to be delivered to the plurality of actuation devices, and wherein the array is further structured to enable variation of said structural configuration from actuation device to actuation device such that the delivery of pressure or vacuum to the plurality of actuation devices results in application of varying magnitudes of mechanical force to the material by means of actuation of the flexible membrane covering said openings based on the structural configuration thereof thereby moving said moving member to compress the material against the weight means.

In a further aspect of the present invention is a method of high-throughput screening responses of a material to mechanical forces of varying magnitudes, characterised in that the method comprises: providing an apparatus of the invention; delivering pressure or vacuum to the apparatus; and measuring the effect of said mechanical forces on the material.

Non-limiting advantages of the apparatus of the present invention include an apparatus that allows high-throughput screening and large out-of-plane actuation distances, which are difficult to achieve in a traditional low-throughput apparatus. Another advantage of the apparatus of the present invention comprises the capability of translating a single input pressure into mechanical forces of varying magnitudes. Yet another advantage of the present invention includes a single apparatus capable of delivering mechanical stimulation and chemical stimulation simultaneously to a material of interest. Yet another advantage of the present invention includes a single apparatus capable of delivering a number of mechanical loading schemes simultaneously to a material of interest. Other advantages of the present invention will become apparent in the description of this invention.

Figure 1A:
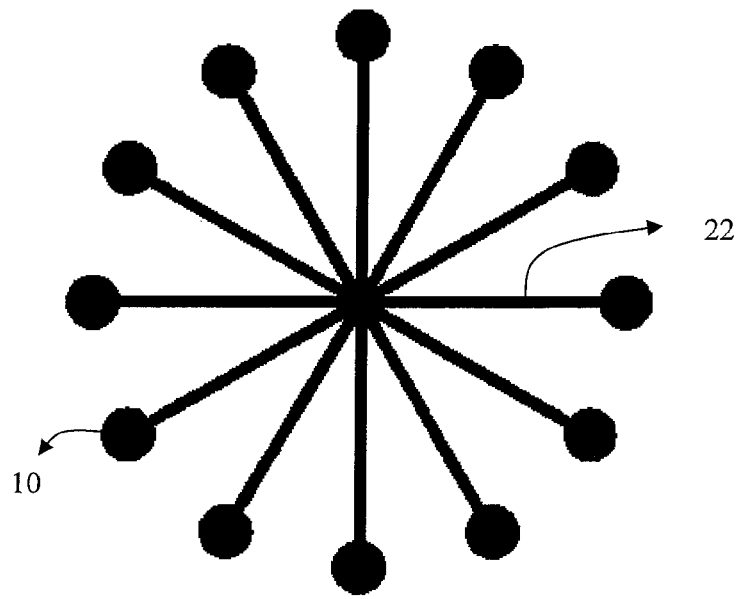
FIG. 1A: illustrates a radial distribution network of channels to supply pressure or lubricant to individual units in the microfabricated array.

In the drawings, one or more embodiments of the present invention are illustrated by way of example. It is to be expressly understood that the description and drawings are only for the purpose of illustration and as an aid to understanding, and are not intended as a definition of the limits of the present invention.

DETAILED DESCRIPTION OF THE INVENTION

The present invention is particularly useful for applying a range of mechanical forces to a material across length scales on the order of micrometers and millimeters. This novel actuation scheme is versatile, and can be used in several configurations and for various purposes. Examples related to uniform and non-uniform substrate-stretch and tissue construct deformation with multiple loading modes are outlined in this disclosed invention. The various embodiments of the invention can be used to apply: (a) non-uniform strain fields of varying magnitudes to a material sample of interest; (b) uniform strain fields of varying magnitudes to a material sample of interest; and (c) compressive stresses of varying magnitudes to a three-dimensional construct.

Commonalities between each of the embodiments will be described first, followed by details relevant to specific configurations.

"Material" as used herein should be understood to indicate any material of interest, including without limitation organic and inorganic materials, films, a combination of multiple substances into an aggregate mixture, cells, tissues, organs, cell cultures.

The major structural components of the apparatus may be made, for example, from polydimethylsiloxane (PDMS, Sylgard 184, DOW CORNING™). The apparatus of the invention may be fabricated using principles of multilayer soft lithography (MSL) in several layers, each layer is formed by casting the liquid prepolymer onto a negative relief mold. The layers are then aligned and bonded to create complex multilevel structures. The integration of other membrane types is also permitted through the use of uncured PDMS as an adhesive layer. Through such bonding techniques, when the material to be tested include cell cultures, membranes of other polymers, including but not limited to polyurethane, polyacrylamide, or a custom-designed polymer membrane can be used as a substrate for the cell culture. The inventors have successfully demonstrated this technique to integrate alternative materials into the PDMS fabrication process with membranes of polydimethylsiloxane and polyurethane. Although not necessary for the utility of the present invention, limiting these membranes to optically transparent materials enables the use of inverted microscopy, a standard tool in biology labs used to visually examine cells and to observe fluorescent reporters and reagents. The transparent feature is advantageous because it enables spatially and temporally heterogeneous cell responses to be visually detected, which is not possible if an assay only measures the end-point response of the entire population, as is typical with HTS.

Figure 1B:
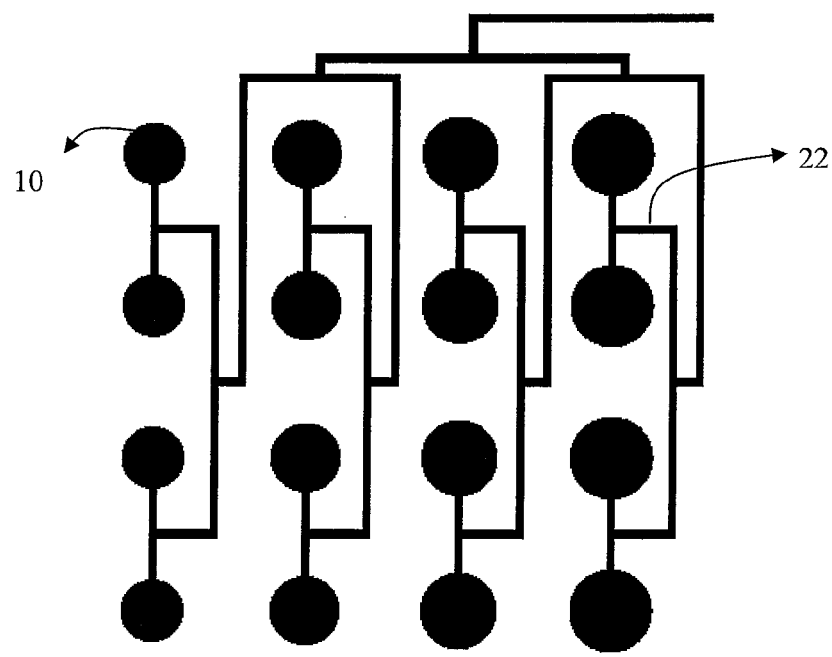
FIG. 1B: illustrates a branching distribution network of channels to supply pressure or lubricant to individual units in the microfabricated array.

The apparatus of the present invention allows for large out-of-plane actuation distances, which are difficult to achieve in a traditional microdevice. Although the magnitude of strain fields can be varied by changing the pressure applied, this would require several external pump systems, to obtain a variety of strain magnitudes in one device. The present inventors have solved the problem of requiring several external pump systems by providing a mechanical design solution. In order to apply a range of mechanical forces across the microfabricated array in each of the embodiments, variations in geometry are employed. A single external pressure and vacuum source is connected to the apparatus of the invention, which by means of a network of microfabricated channels delivers pressure or vacuum to each of the individual units (also known as "actuation devices") in the array. FIG. 1A and FIG. 1B illustrate examples of such pressure delivery channel network 22. Variations in geometric dimensions of individual units 10 in the array are used to vary the amount of mechanical force generated by that actuation device 10. The mechanisms for generating the types of mechanical forces are outlined in the following embodiments.

In one aspect the present invention is an apparatus for applying mechanical forces of varying magnitudes to a material characterized in that the apparatus comprises: at least one array defining a surface and a plurality of actuation devices disposed thereon, each of said actuation devices having a structural configuration, said structural configuration including an opening; and a flexible membrane fixed to the surface and covering said opening, said membrane having an upper surface that permits attachment of the material thereto, wherein the array is structured to enable pressure or vacuum to be delivered to the plurality of actuation devices, and wherein the array is further structured to enable variation of said structural configuration from actuation device to actuation device such that the delivery of pressure or vacuum to the plurality of actuation devices results in application of varying magnitudes of mechanical force to the material by means of actuation of the flexible membrane covering said openings_based on the structural configuration thereof.

Figure 2:
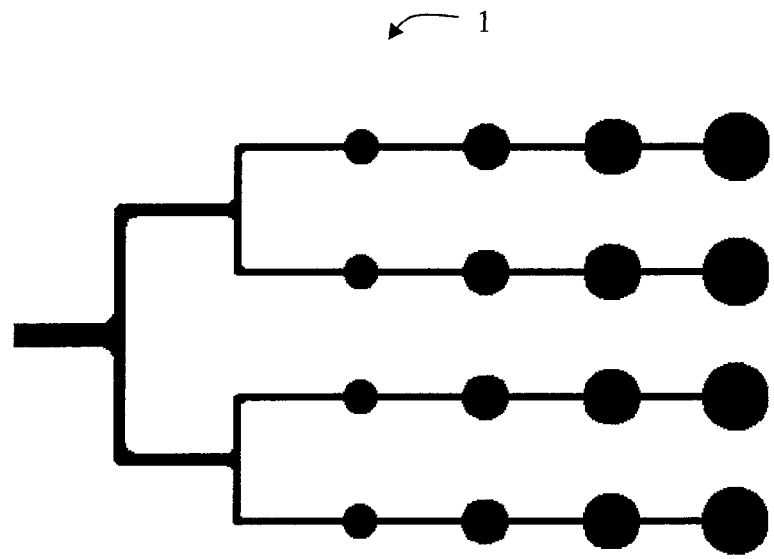
FIG. 2: top-down schematic of the non-uniform substrate strain embodiment of the invention, illustrating the varying size of the actuation cavities across the array.
Figure 3:
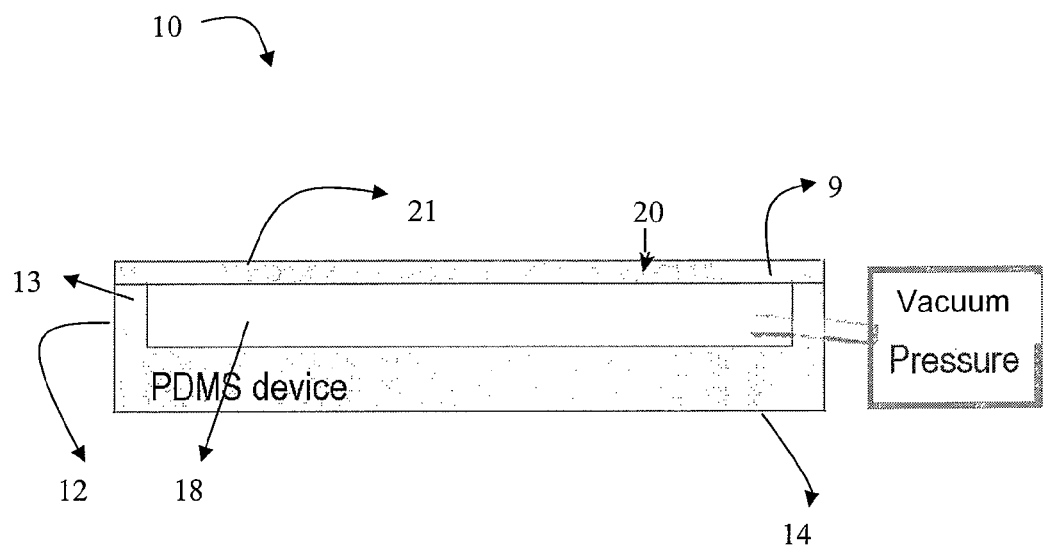
FIG. 3: cross-sectional view of non-uniform substrate strain embodiment of the invention, illustrating the actuation cavity, and polymeric thin film.
Figure 4:
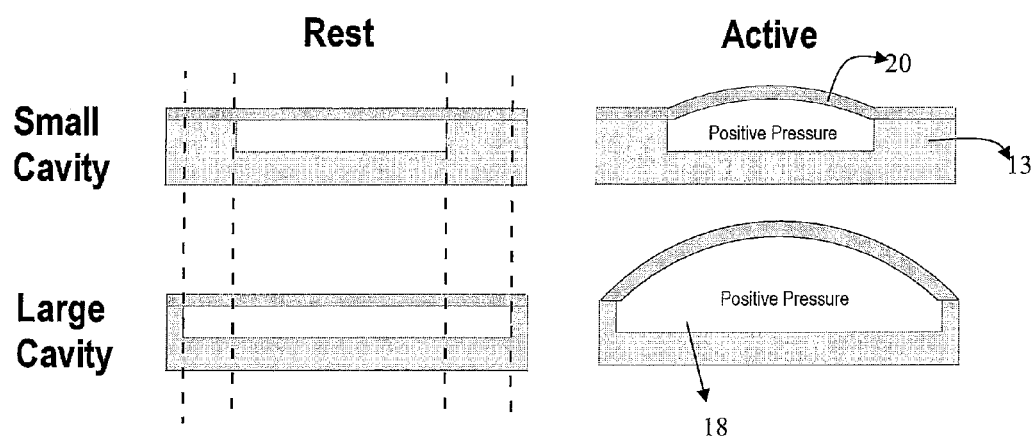
FIG. 4: demonstrates the working principles of this embodiment of the invention. Increases in actuation cavity size create different vertical displacements.
Figure 5:
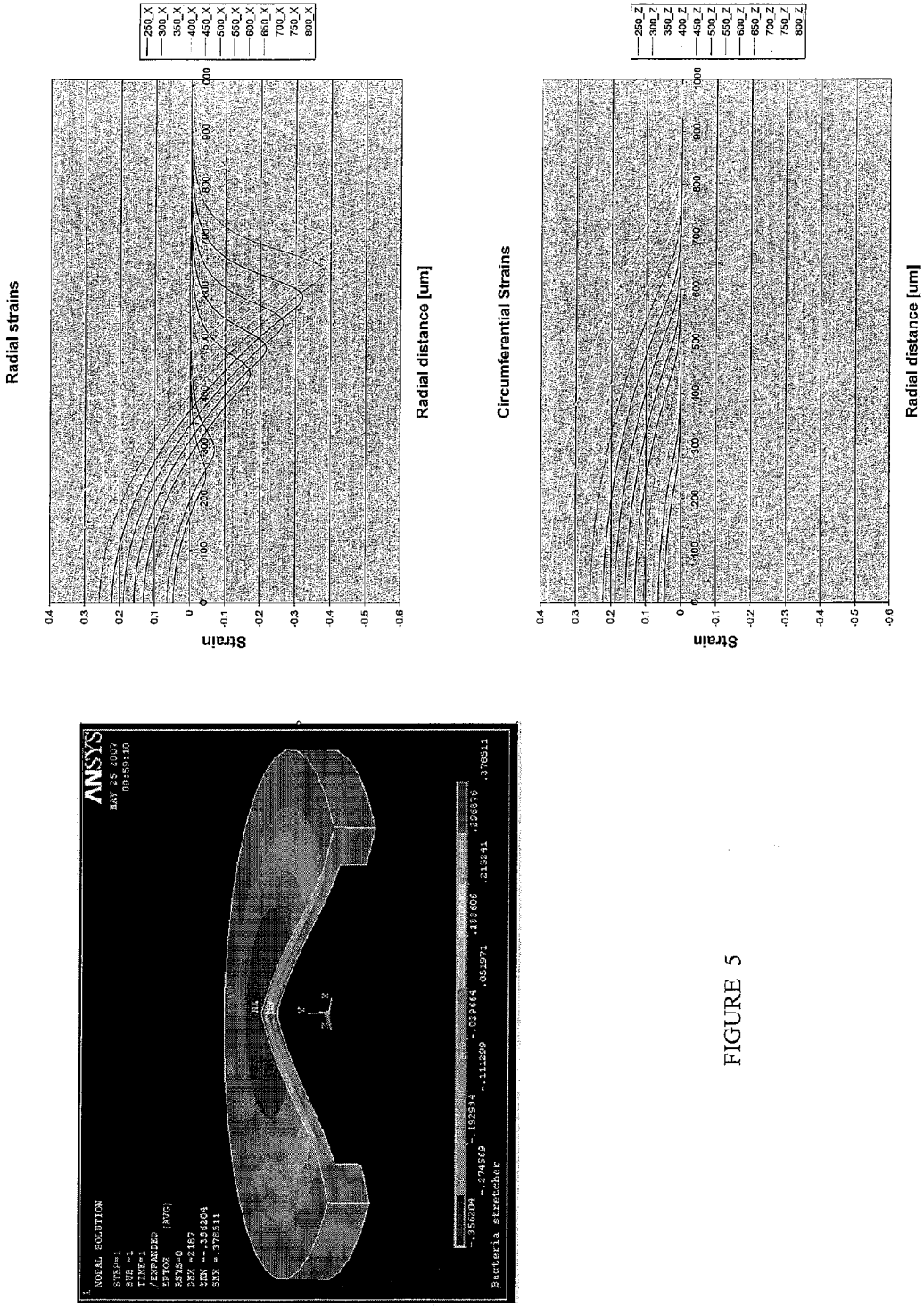
FIG. 5: Finite element simulations displaying radial and circumferential strains obtained across the radius of bulged films of different sizes.

A top-down schematic of the array 1 is shown in FIG. 2. A cross-sectional view of a single actuation device 10 in the array 1 is provided in FIG. 3, showing the single unit 10 in the array 1 at rest. The actuation device 10 comprises a structural configuration including an opening 9. The actuation device 10 includes an actuation cavity 18 including a cavity wall 12 having a thickness 13 and a bottom wall 14. A flexible membrane 20 is fixed to the array surface (not shown) and covering the opening 9. The flexible membrane 20 has an upper surface 21 that permits attachment of a material of interest. In one aspect the flexible membrane 20 comprises a thin polymer film. Applying a positive or negative pressure within the actuation cavity 18 bows the thin film 20 upwards or downwards. FIG. 4 illustrates the use of variation in geometry to provide different non-uniform strain fields. The left side of the figure shows cross-sectional views of actuation devices with two dimensions of the actuation cavity 18. A pair of dimensions are used merely for illustration purposes. The right side of the figure shows the effect of varying actuation cavity 18 geometry on the bending applied to the thin polymeric film 20 under the same positive pressure. By decreasing the thickness 13 of the cavity wall 12 the unsupported membrane 20 over the actuation cavity 18 increases, the stiffness of that membrane 20 decreases, and the membrane 20 is bowed further. FIG. 5 shows finite element simulation results for various actuation geometries of a circular unit. The results show non-uniform strain fields in the radial and circumferential directions of the polymeric film 20. The finite element analysis shown in FIG. 5 simulates a circular membrane being deformed by a pressure applied beneath it. These simulations were conducted using the same applied pressure for circular membranes of various dimensions, ranging from diameters of 500 μm to 1.6 mm in 100 μm increments. A three-quarter view of a representative simulation is provided to better illustrate the function of this embodiment. Radial and circumferential strains across the surface of the membrane are presented in graphical form. The results indicate non-uniform strain fields across the surface of the membrane, with unequal radial and circumferential components of the applied strains.

Figure 6:
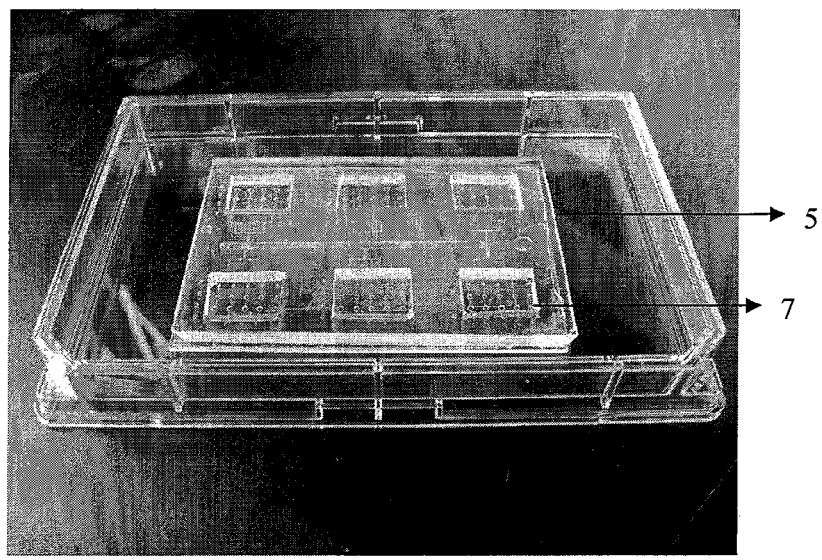
FIG. 6: Picture of sample microfabricated device for the substrate strain embodiment of the invention.

To demonstrate the applicability of the first embodiment of the present invention, FIG. 6 depicts an apparatus 5 of the present invention having circular actuation cavities 18, however other obvious patterns may be used (FIG. 6). In the apparatus of FIG. 6, the circular actuation cavities 18 are used to provide strain fields similar to those shown in the finite element simulations of FIG. 5. However, various strain fields can also be generated by changing the shape of the actuation cavity 18. This requires no change to the actual manufacturing process of the apparatus, and can be achieved by modifying the template used to build the apparatus. The sample apparatus 5 of FIG. 6 shows six isolated, identical groups, each of which contains twenty mechanically active actuation sites 10. By applying a single positive pressure to the entire apparatus 5 (not shown), the channel network 22 delivers the pressure from a source of pressure to each of the mechanically active actuation sites 10 in all the isolated groups, bowing the membranes, the out-of-plane displacement of which is commensurate with the actuation cavity geometry. In this example, polyurethane films are bonded to the surface of the PDMS device.

Figure 7:
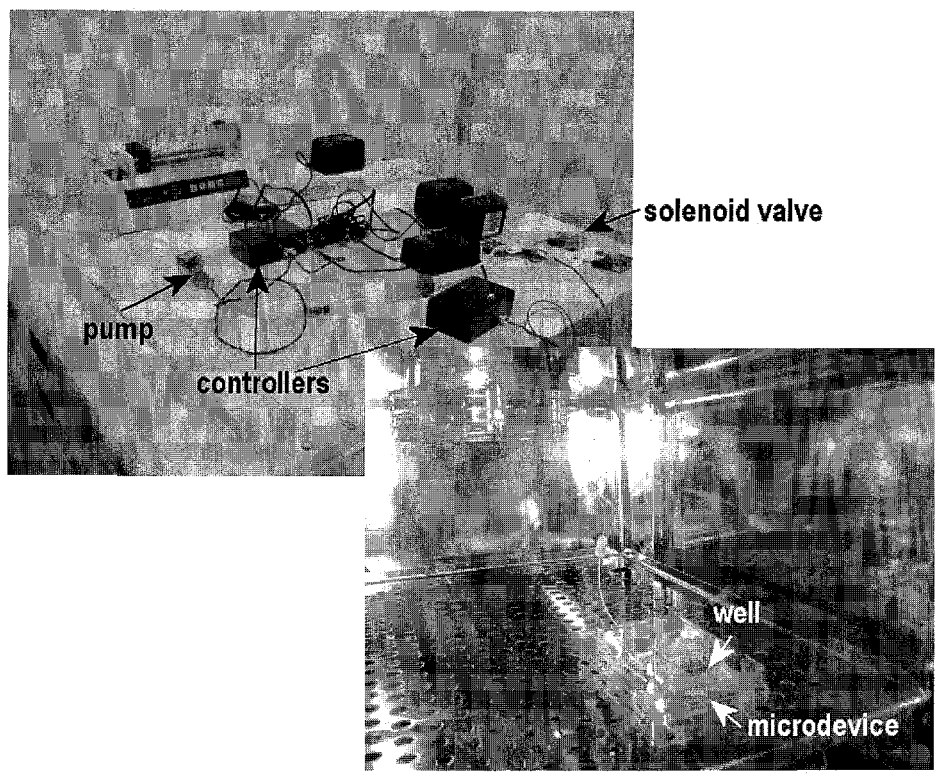
FIG. 7: Image of the non-uniform substrate strain microsystem in the cell culture incubator, with associated peripheral devices (including pump, valves and controllers).

In one non-limiting example the experimental setup of FIG. 6 is being used to apply a range of non-uniform strain fields to adherent biological cells cultured on the surface of the array 1. The setup shown in a cell culture incubator is shown in FIG. 7. The well 7 shown in the apparatus 5 is used to hold cell culture media, which allows the array 1 in the apparatus 5 to respond to a specific set of chemical factors in the culture media. In this specific example extra-cellular matrix (ECM) proteins are deposited by adsorption on the surface of the polyhrethane films—these ECM proteins can include but are not limited to collagen (Types I-IV), fibronectin, laminin, vinculin and heparin. Each array 1 in each apparatus 5 can be patterned with a different ECM protein at different concentrations. A further extension to this example would be achieved by employing well-established techniques for protein patterning, such as those described in R. S. Kane et al., "Patterning proteins and cells using soft lithography," *Biomaterials*, vol. 20, pp. 2363-2376, December 1999, which can be used to deposit on each actuation site 10 in the array 1 various types and concentrations of proteins. This will allow control over extra-cellular matrix composition for individual bioreactor units.

Figure 8:
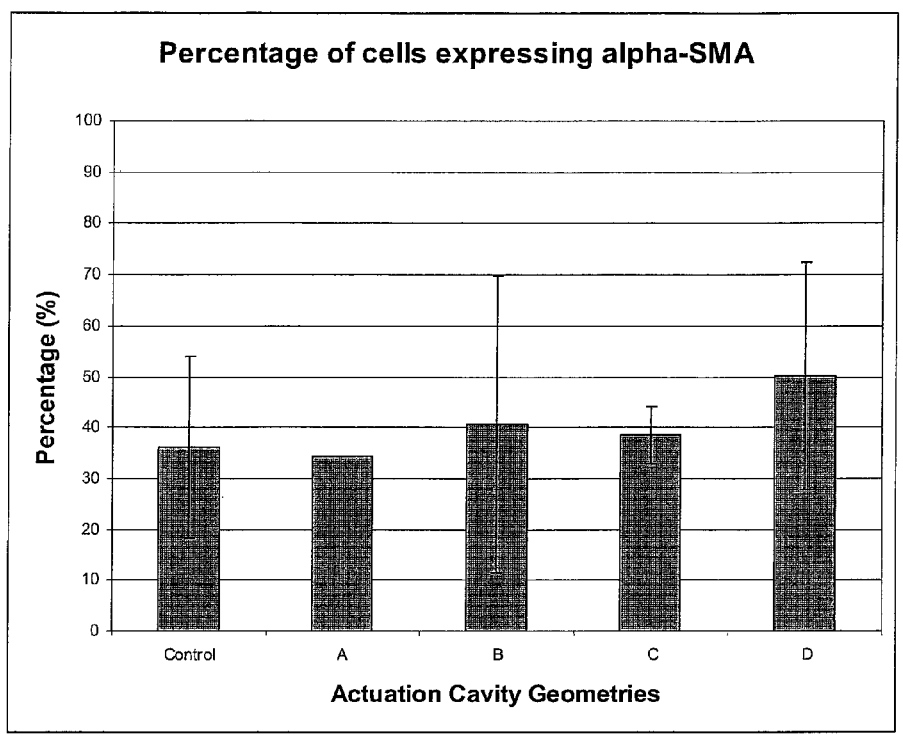
FIG. 8: Graph presenting results for percentage of cells expressing alpha-smooth muscle actin across the mechanically active culture regions of the array.

Specific to this particular experiment, subcultured porcine aortic valvular interstitial cells (PAVICs) isolated from pig heart valve leaflets were seeded on the surface of the array and allowed to attach and spread without mechanical stimulation. This was achieved using standard cell culture techniques. Initial experiments involved applying a cyclic mechanical deformation to the film upon which the cells were attached, over a period of two days. Analysis of the effects of mechanical stimulation involve staining the cells for the presence of a-smooth muscle actin (αSMA), a mechanosensitive cytoskeletal protein. Fluorescent imaging and analysis yielded results shown in FIG. 8 for the percentage of cells expressing αSMA from the total population on each experimental unit. This experiment demonstrates the practicality of collecting data on biological cell response through fluorescent imaging techniques. Various other combinations of ECM proteins, culture media composition and mechanical stimulation to tease out differences in biological activity in response to varying non-uniform strain fields may be studied with the use of the apparatus of the present invention.

The apparatus of the present invention is useful to probe all adherent cell types, including but not limited to heterogeneous cell populations, stem cells, progenitor cells, primary isolates, and cell lines, which has broad scope for use in experiments in biomedical research. Possible applications include determining the effects of various external stimuli in combination with non-uniform cyclic mechanical strain on cells, including but not limited to levels of drug uptake, efficacy of gene therapy, receptor formation, cytokine production, proliferation, apoptosis, structural reorganization, morphology, gene and protein expression, and differentiation on a large number of cell types from various model organisms.

The apparatus of the present invention could also be used to applying varying non-uniform strains to native tissue samples, cells encapsulated in a thin membrane, or as a material testing unit for thin polymer films. This last application is of particular relevance to the materials science community, looking for novel experimental methods to test mechanical properties of thin films, membranes and biological tissue samples, which have been shown to have different properties than when in their bulk forms. Previously patented techniques include mechanical characterization through laser excitation (U.S. Pat. No. 5,672,830); microindentation using piezoelectric positioners (U.S. Pat. No. 5,553,486). These techniques are serial in nature, and cannot collect data quickly. A more recent attempt to create a high-throughput system has been patented (U.S. Pat. No. 6,772,642), in which an array of samples is tested by a positionable force generator. However, data collection is still serial.

This potential setup has the advantage of higher throughput over current attempts—a series of data for responses to a range of mechanical forces is collected simultaneously. In one aspect a sample of the material of interest, such as a thin membrane of the material or biological tissue to be studied is bonded by an adhesive agent to the surface of an array and suspended over a series of actuation devices with increasing radii. By applying a controlled positive pressure and determining the vertical displacement of the membrane, the stiffness and Young's modulus of the film can be determined. Increasing the pressure to breakage determines ultimate stress properties of the material. Continuous cycling of the pressure source determines fatigue, elasticity and plasticity. Because of the device throughput, a great deal of data for various stresses can be obtained simultaneously.

Figure 9:
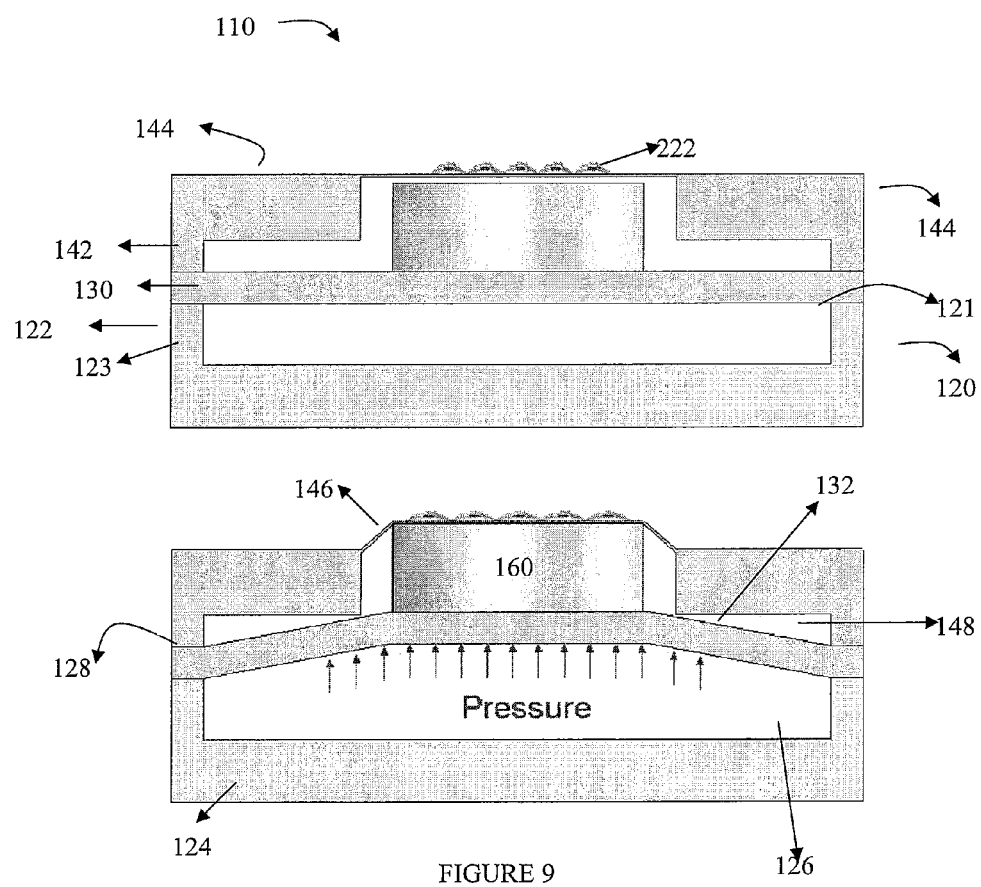
FIG. 9: illustrates the working principles of the uniform substrate strain embodiment of the invention. As pressure is applied to the actuation cavity beneath the support layer, the loading post is driven upwards into the culture membrane.

FIGS. 9 through 13 depict the mechanical principles of the second embodiment of the present invention. With reference to FIG. 9, each actuation device 110 comprises: a base 120 including a first opening 121 and comprising a first actuation cavity 126 including a cavity wall 122 having a thickness 123 and a bottom wall 124. The said cavity wall 122 has an upper end 128 configured to fix a flexible actuation membrane 130 that covers the opening 121, said actuation membrane 130 having an upper side 132; an upper structure 140 comprising a side wall 142 that ends on the array surface 144, a second opening 146 and a second cavity 148. A substrate membrane 220 is fixed to the surface 144 and covers the second opening 146. The substrate membrane 220 is configured to support a material of interest 222 across the opening 146; a post 160 extending from the upper side 132 of the actuation membrane 130 into the second cavity 148 towards the second opening 146.

As a non-limiting example, FIG. 9 demonstrates the principle for applying a substrate-induced deformation to adherent cells in a two-dimensional culture. The upper diagram illustrates the cross-sectional view of a single unit of the actuation device 110 at rest. The actuation membrane 130 then bows upwards, driving the post 160 up into the substrate membrane 220, atop which adherent cells 222 are cultured. The culture membrane 220 then slips and stretches over the raised loading post 160, creating a uniform strain field, the features of which depends on the geometry of the loading post 160. Examples include but are not limited to: a circular post, which will create a cylindrical equibiaxial strain field; a square post which will create an equibiaxial strain field; and a rectangular post which will create an anisotropic biaxial strain field, approaching uniaxial strains. As in the previous embodiment, this embodiment of the system can be used to probe all adherent cell types, including but not limited to heterogeneous cell populations, stem cells, progenitor cells, primary isolates, and cell lines.

Figure 10:
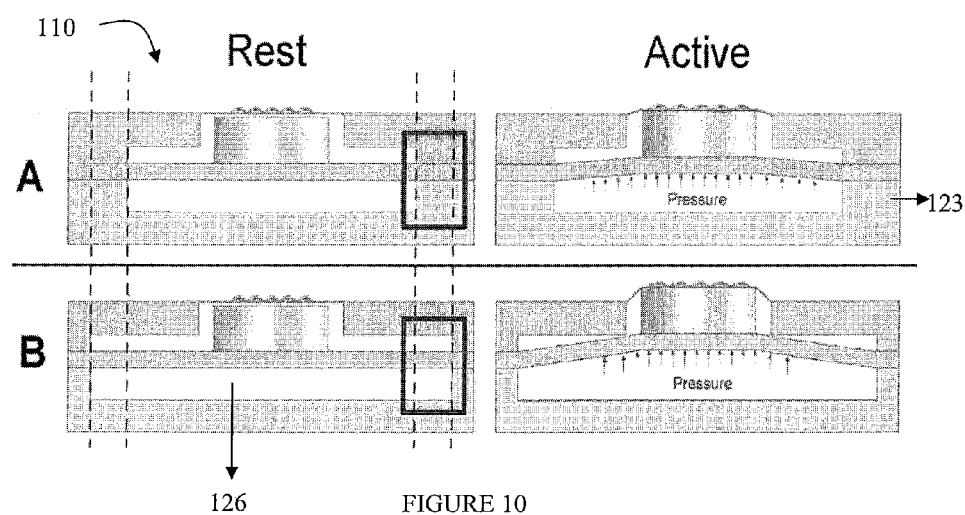
FIG. 10: demonstrates the working principles of this embodiment of the invention. Increases in actuation cavity size create increases in vertical displacements of the loading post, for a given applied pressure.
Figure 11A:
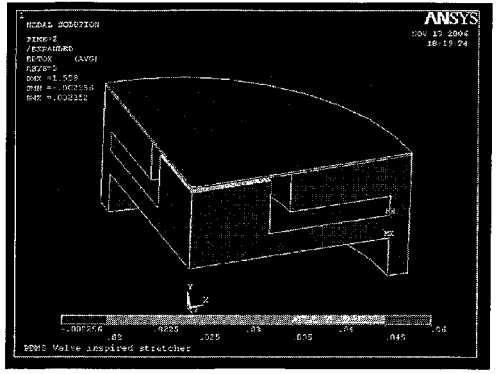
FIG. 11A-F: Sequence of images from the finite element analyses performed for this embodiment of the device.
Figure 11B:
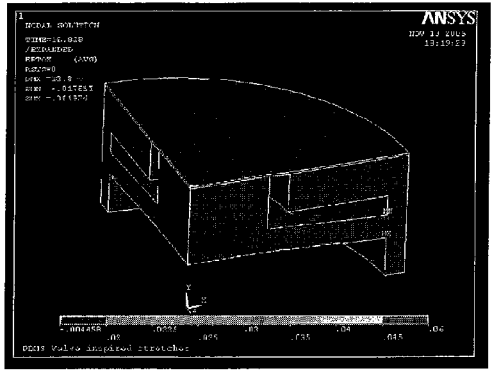
Figure 11C:
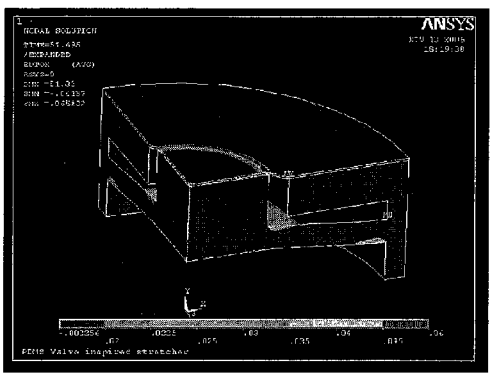
Figure 11D:
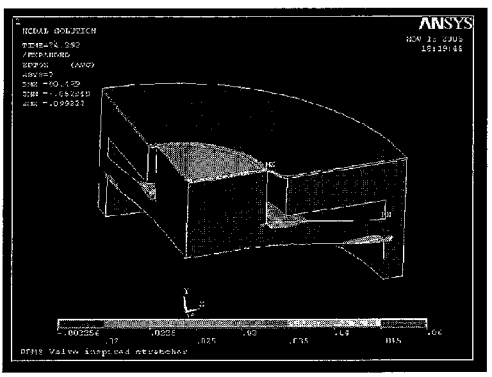
Figure 11E:
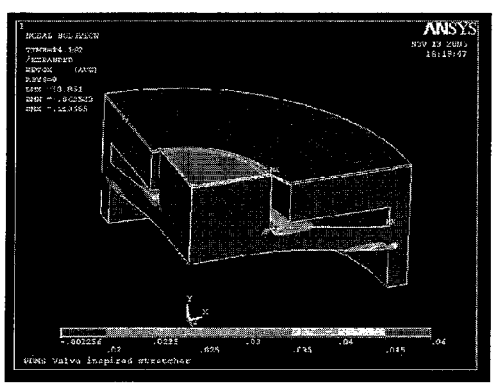
Figure 11F:
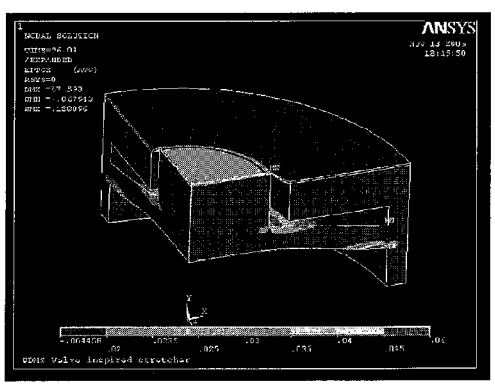

The use of varying geometry to change mechanical forces applied is demonstrated in FIG. 10, which uses the substrate-stretch embodiment of this invention as a descriptive aid. The right half of the image depicts a cross-sectional view of the actuation device 110 with no external positive pressure applied (at rest). The device 110 of lower quadrant of FIG. 10 features a much larger size actuation cavity 126 than the upper quadrant of FIG. 10. As the size of the unsupported actuation membrane 130 increases, the stiffness of the membrane 130 decreases, and the post 160 is vertically displaced further. In this way, by varying the lateral geometry of the system, the vertical actuation distance is varied for a fixed applied pressure, and hence the strains generated in the culture membrane 220 are also varied. The magnitudes of generated strain fields are limited by the material's ultimate elastic strain: preliminary finite element simulations indicate a range from 0-5% strain for our specific initial design—however, based on experimental results, the design can be realistically adjusted to provide mechanical stimulation ranging from 0 to approximately 20% strain.

Figure 12:
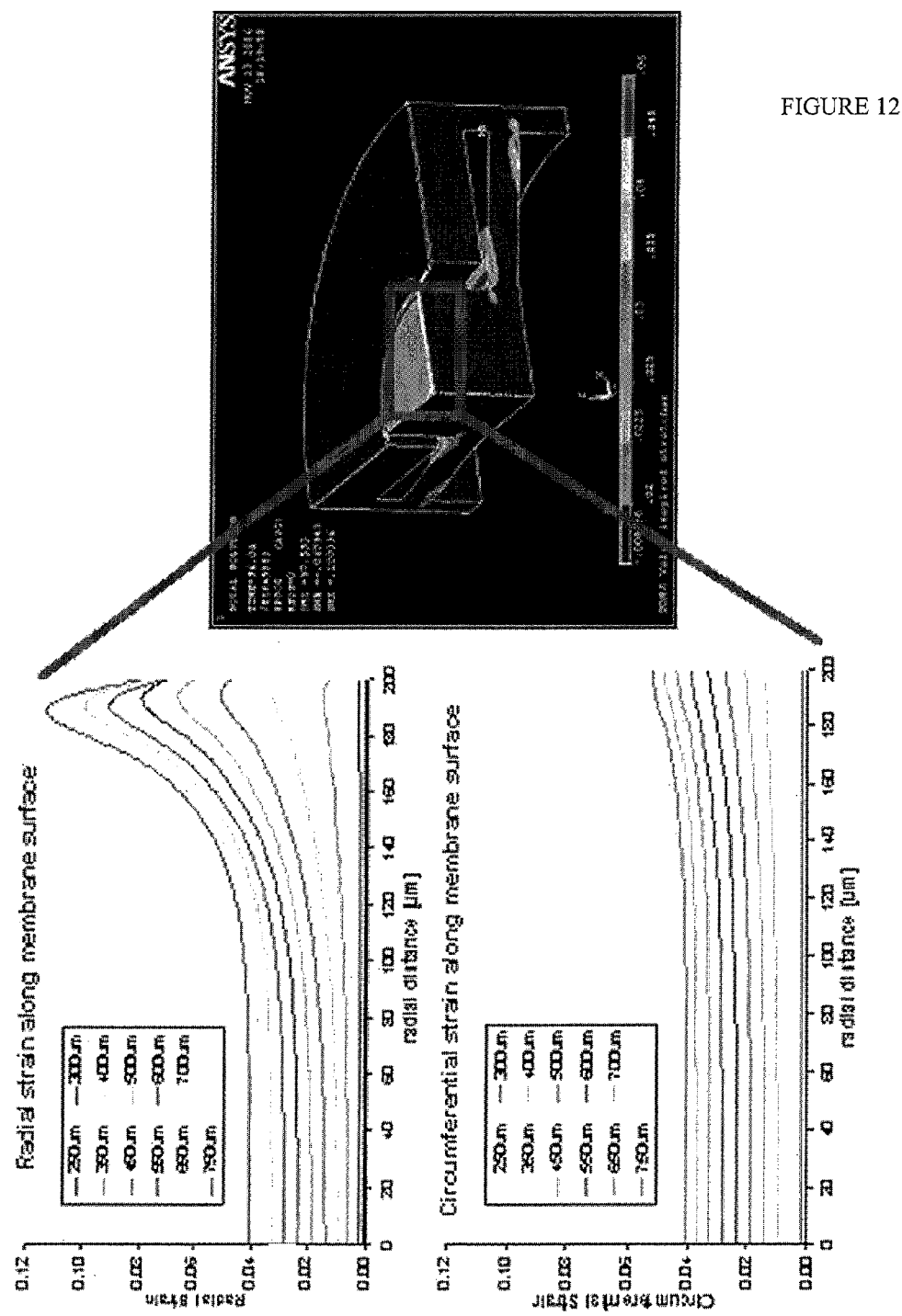
FIG. 12: Graphical representation of the radial and circumferential strains obtained across the surface of the device, for different sizes of actuation cavity, for a circular loading post profile.
Figure 13:
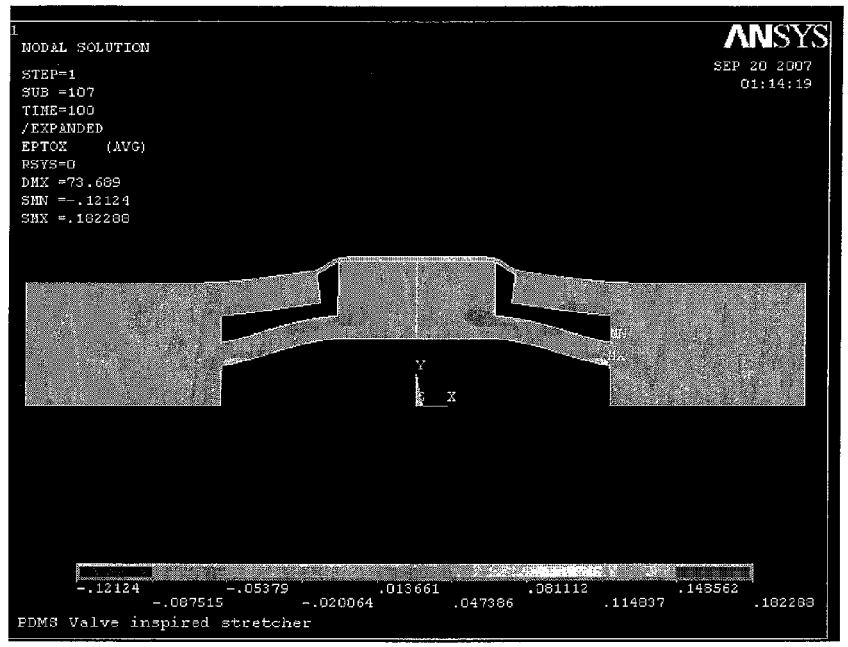
FIG. 13: Finite element simulation results for a square loading post profile.
Figure 13:
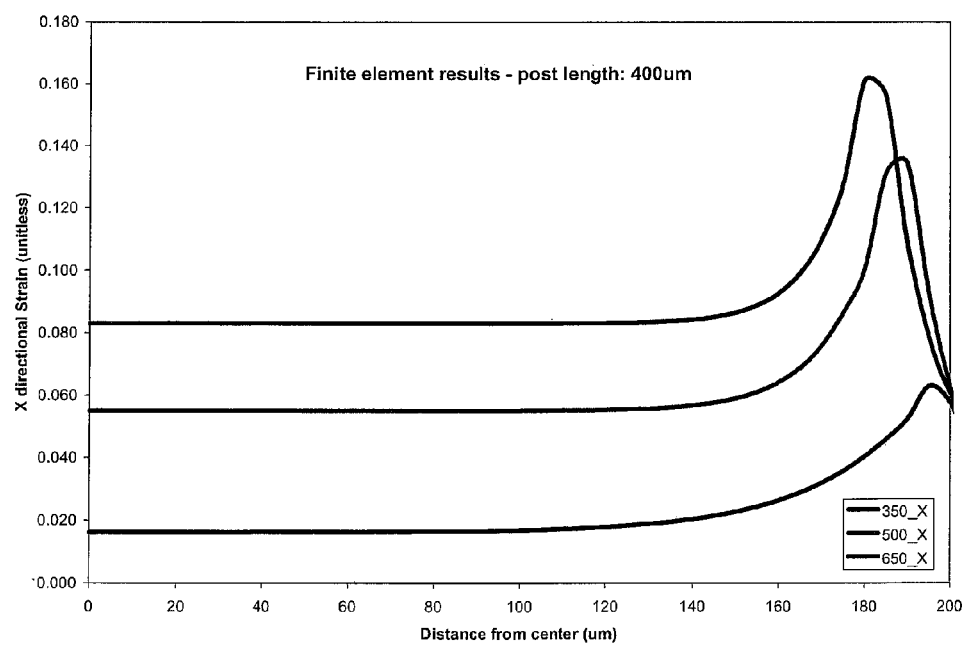

To better illustrate the mechanical actuation of the system, a sequence of images taken from a finite element simulation have been included. The simulation depicts a circular loading post as an example, in a substrate-stretch configuration. The simulation assumes frictionless interaction between the post and the membrane. The images shown in FIG. 11A-F show how the post is driven up into the membrane, causing stretch to occur. Note that this sequence is not indicative of any specific elapsed time. The quantitative results for this simulation are shown in FIG. 12. The radial and circumferential strains along the membrane surface are graphically displayed. This exercise confirms an equibiaxial stretch for this particular situation, and indicates a region of uniform strain within the radius of the loading post. Two-dimensional simulations were also performed for a square post geometry: results for a section of square post geometries indicate similarly uniform results, and are shown in FIG. 13.

The fabrication process for this second embodiment of the device 110 may be based on known standard processes of multilayer soft lithography. No claims of novelty are made on these techniques. Essentially, a negative relief mold is created for each layer of the device, again by standard processes. Two examples are provided for illustration and not, limitation. The first is the use of Microchem's SU-8 negative photoresist to pattern molds of various thicknesses. Alternatively, silicon micromachining in a silicon-on-insulator wafer can be used with Deep Reactive Ion Etching to create molds with vertical side walls and flat bottoms. A liquid prepolymer (for example, PDMS) is poured over the mold and temperature-cured. The PDMS can then be peeled off the mold and it retains the microscale features. PDMS can also be spin coated on a second mold, resulting in a very thin patterned film. Alternatively, the technique developed by Jo et al., (B. H. Jo, L. M. Van Lerberghe, K. M. Motsegood, and D. J. Beebe, "Three-dimensional micro-channel fabrication in polydimethylsiloxane (PDMS) elastomer," *Journal of Microelectromechanical Systems*, vol. 9, pp. 76-81, March 2000.) can be used in which the liquid polymer layer is squeezed in a mechanical clamp, creating a very thin film. These films are then aligned using a micromanipulator and bonded together by treating the surfaces with a corona discharge unit.

One aspect of novelty is introduced into the fabrication process. When bonding the culture membrane to the first three layers of the device, in order to prevent the partially cured culture membrane from bonding to the post, a vacuum is applied to the actuation membrane, sucking the posts away from the culture membrane. The membrane is then bonded, and cured while the actuation membrane is under vacuum. Low viscosity oil is heated to further reduce viscosity and then flushed between the post and the actuation membrane, providing a lubricating layer, and preventing excessive friction. When the vacuum is released the loading post returns to its original position, unattached to the culture membrane, and lubricated by the oil.

Figure 14A:
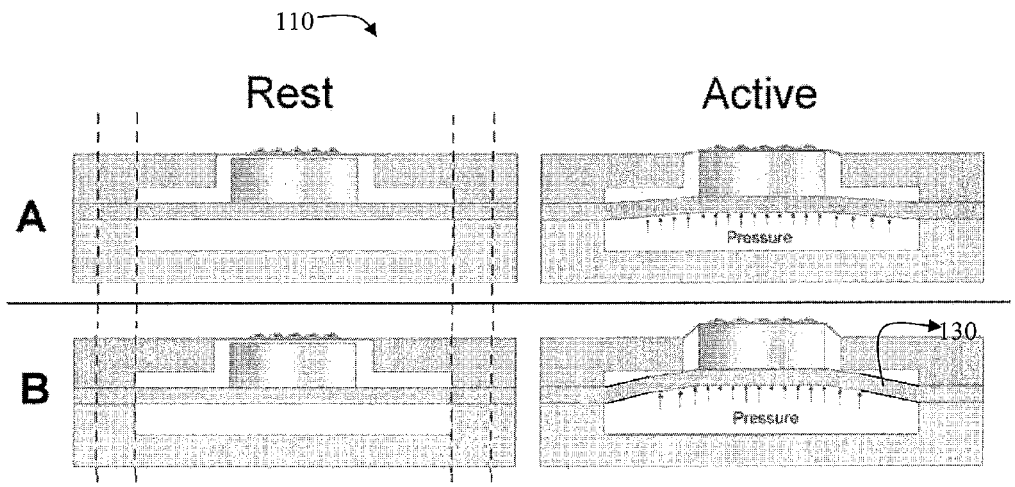
FIG. 14A-E: demonstrates variations in various segments of the material area.
Figure 14B:
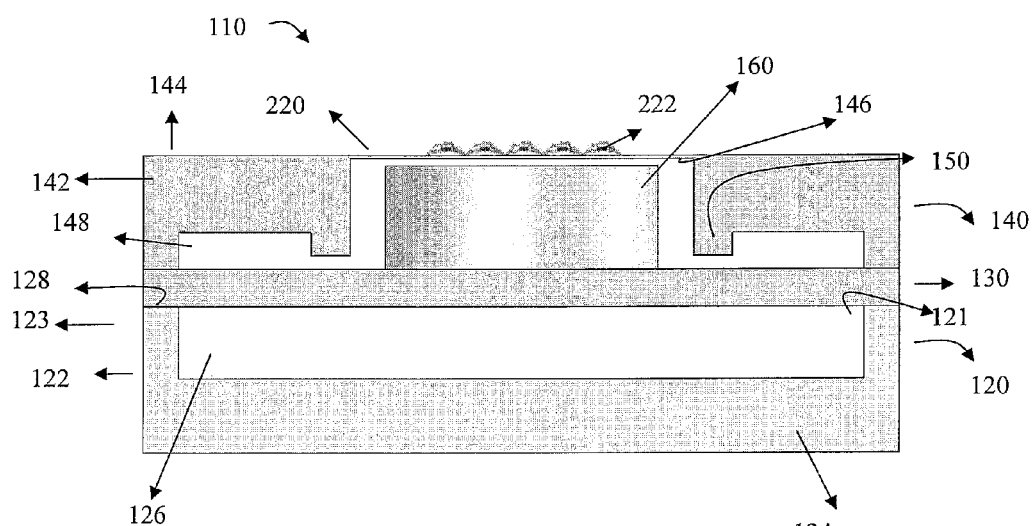
Figure 14C:
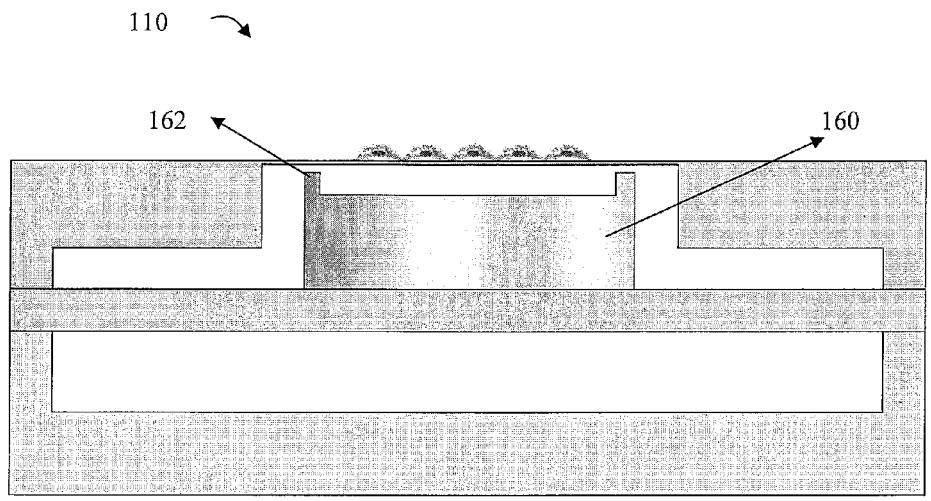
Figure 14D:
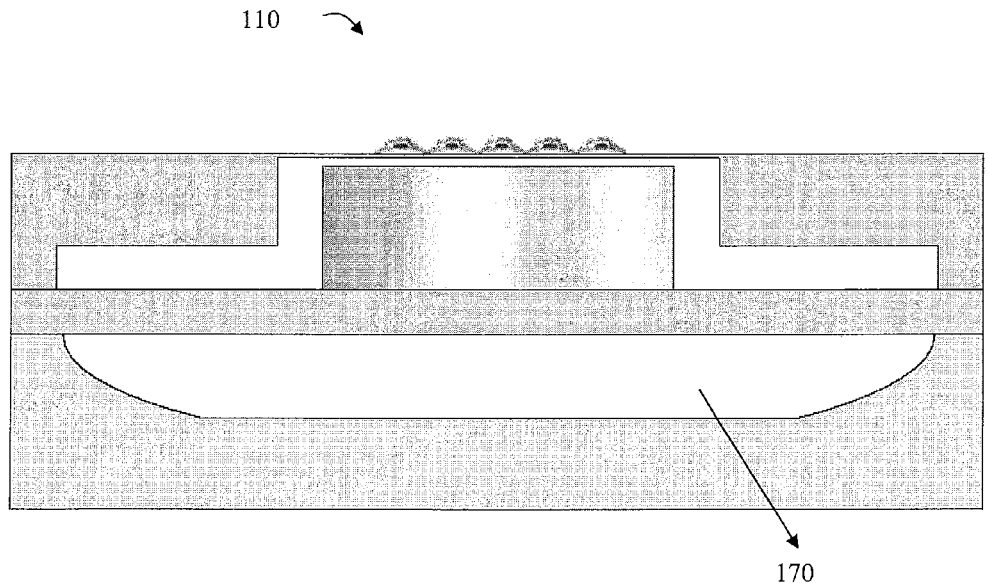
Figure 14E:
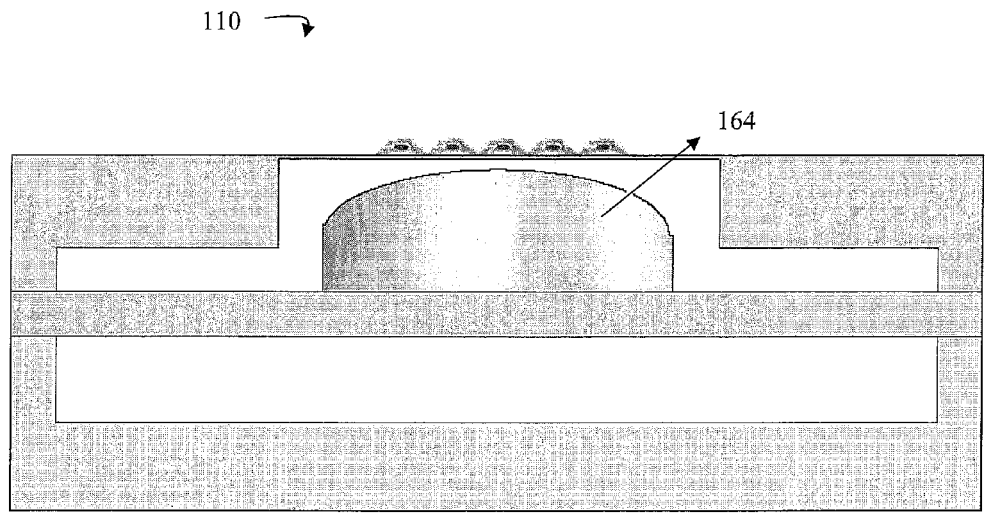

To illustrate the range of other design considerations encompassed by the present invention, a number of modifications have been made to the design of the device 110, and shown in FIG. 14A-E. In FIG. 14A, a different material is used for one of the structural layers of the device 110. FIG. 14B shows a modified structural configuration in which structural means or notches 150 extend from surface 144 of the array are used to limit vertical movement of the actuation membrane 130. FIG. 14C incorporates the use of a 'lip' 162 on the loading post 160 to reduce the friction between the post and the culture membrane 220, by reducing the total area of contact. FIG. 14D demonstrates one of the possibilities of actuation cavity geometry 170 achieved through a different fabrication process. FIG. 14E shows a post 164 profile that is different in the vertical as well as the planar directions.

Figure 15A:
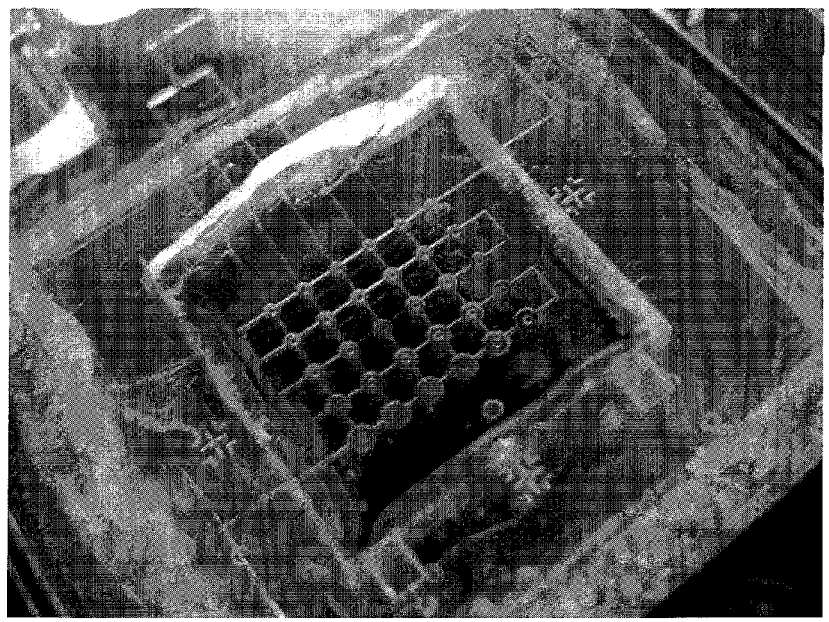
FIG. 15A: illustrates the 5×5 array produced as an example of this embodiment of the invention.
Figure 15B:
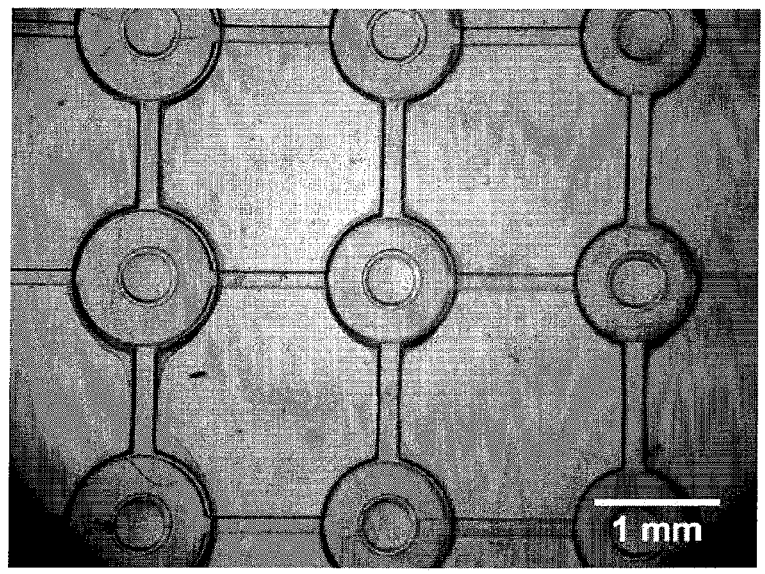
FIG. 15B: top down view of the example array fabricated as an embodiment of this invention.
Figure 15C:
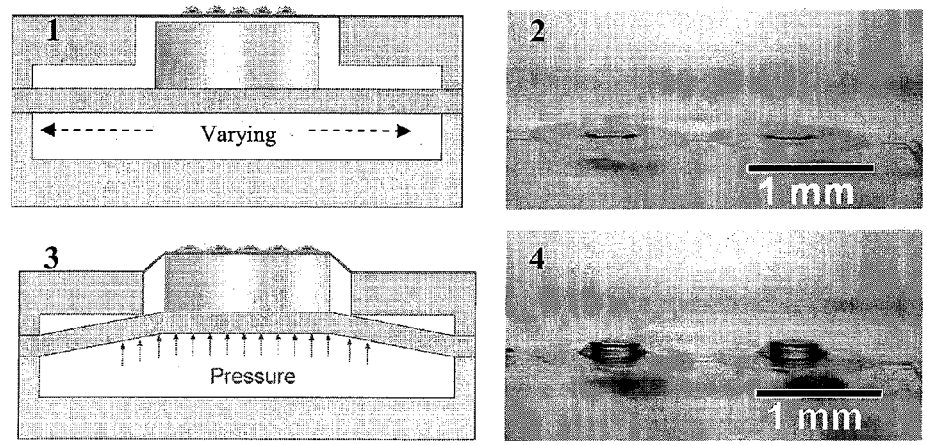
FIG. 15C: images of the device at rest and while actuated.
Figure 16:
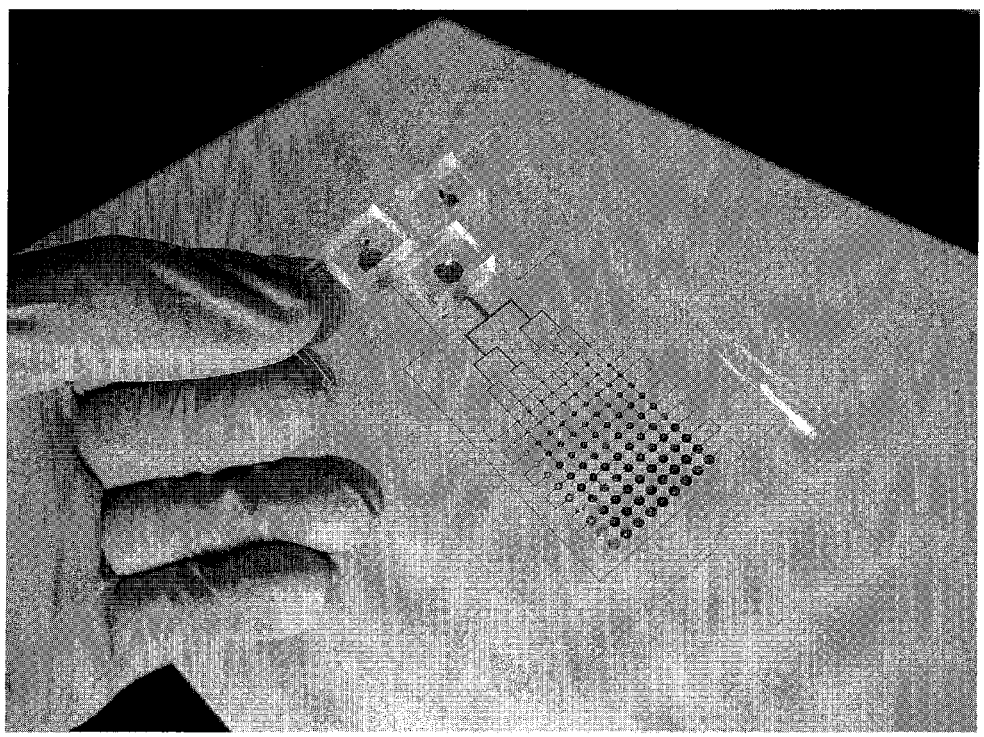
FIG. 16: example of a larger array for the uniform substrate-strain embodiment of this invention.
Figure 17:
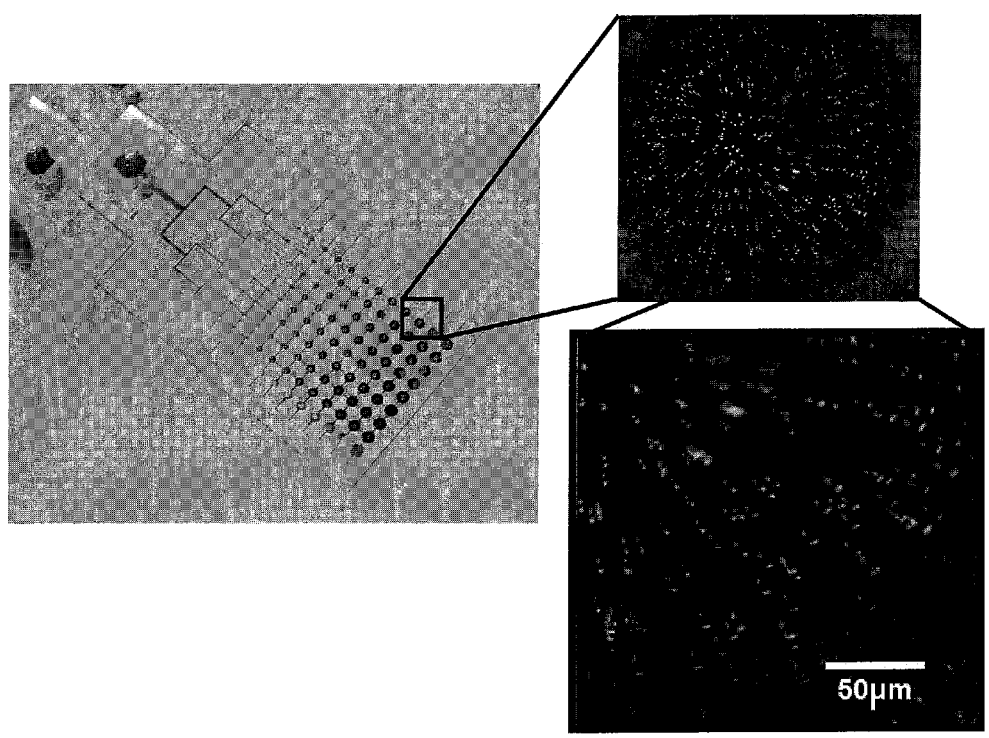
FIG. 17: illustrates the displacement of fluorescent beads on the surface of the membrane, used to calibrate the strains produced by the device.

To demonstrate the practicality and feasibility of such a system, a sample 5×5 array of individual units was constructed (FIG. 15A). Actuation of the structure is demonstrated in FIGS. 15B and C. Arrays with larger number of units can easily be fabricated (FIG. 16), but for demonstration and initial experimentation purposes, a 5×5 array was used. This array has been successfully constructed with a polydimethylsiloxane culture layer, or with a polyurethane culture layer, using bonding techniques discussed previously. The density of the experimental units is equivalent to that of a 1536-well plate, which can provide a 256-fold increase over currently available substrate-stretching equipment.

Figure 18:
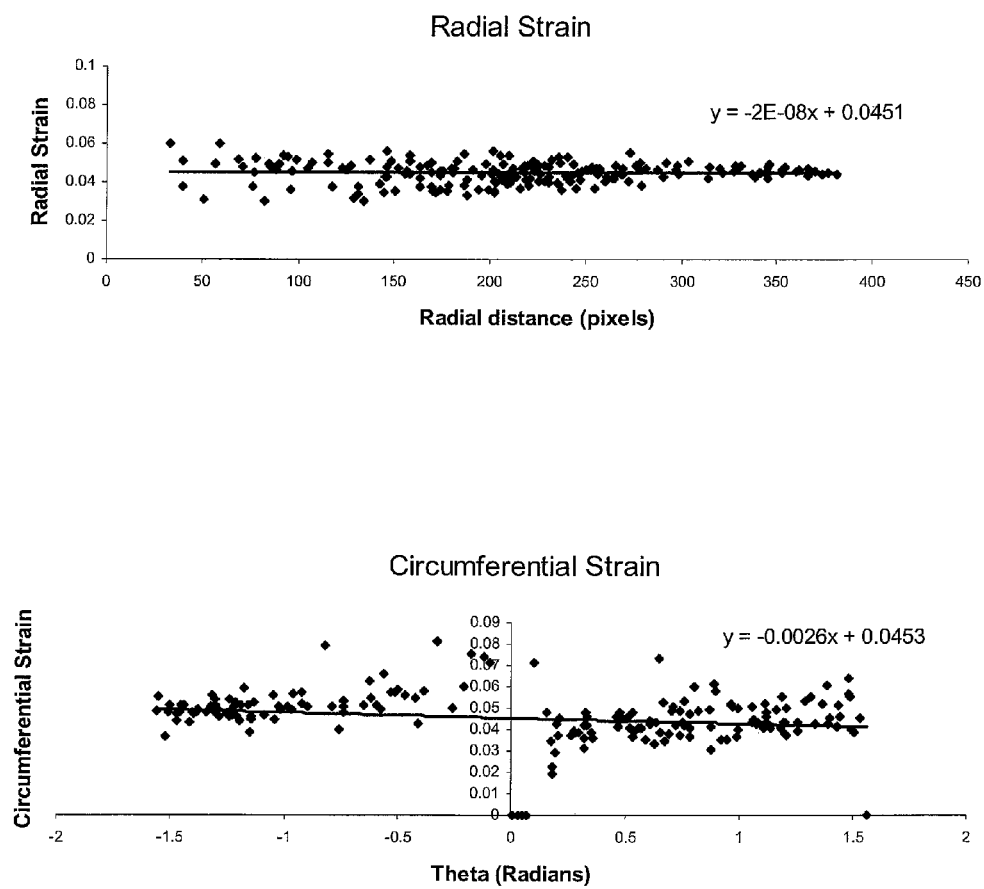
FIG. 18: Graph representing radial and circumferential strains results obtained from analysis of the fluorescent bead displacements.
Figure 19:
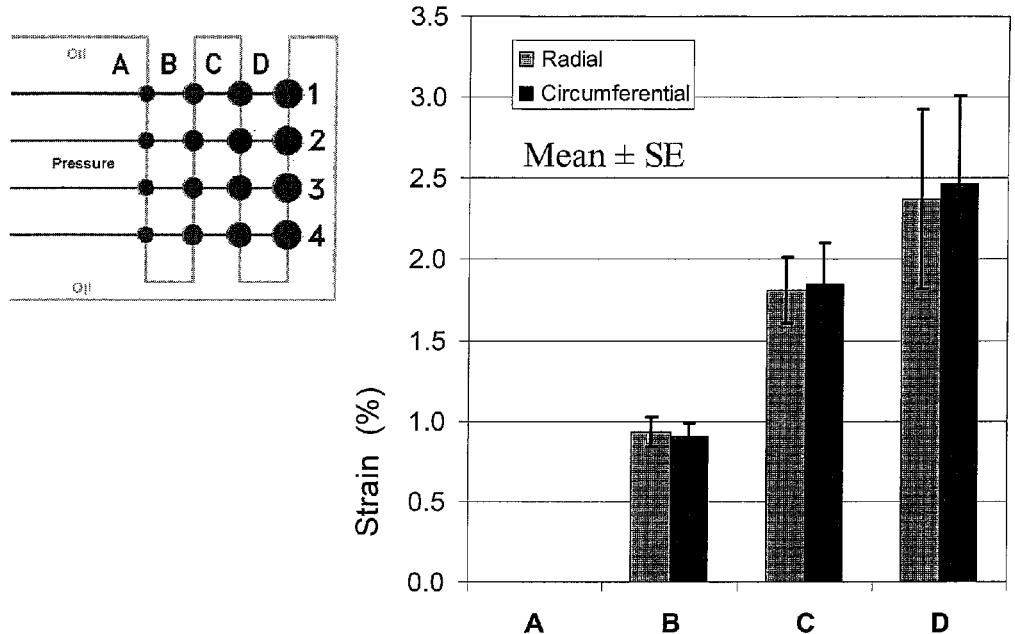
FIG. 19: Graph presenting results for the fluorescent bead calibration across the array.

In order to calibrate the strains exerted by the device, fluorescent beads, 1 micron in diameter were deposited on the surface, and imaged in a standard fluorescent microscope. The array was then actuated, and the locations of the fluorescent beads tracked, using standard image analysis techniques. The radial and circumferential strains across the surface of the membrane were then extracted from the raw displacement data, and the results plotted in FIGS. 18A and B. The graphs indicate uniform strains across the surface, and an equibiaxial condition (equal radial and circumferential strains). Deviations from uniformity can be attributed to errors in measurement of the fluorescent bead positions. The nominal strain values for the radial and circumferential axes were then tabulated for each of the differently-sized units in the array. The results for a polyurethane membrane are shown in FIG. 19, and indicate an increasing strain level across the array, as demonstrated by simulation.

Figure 20:
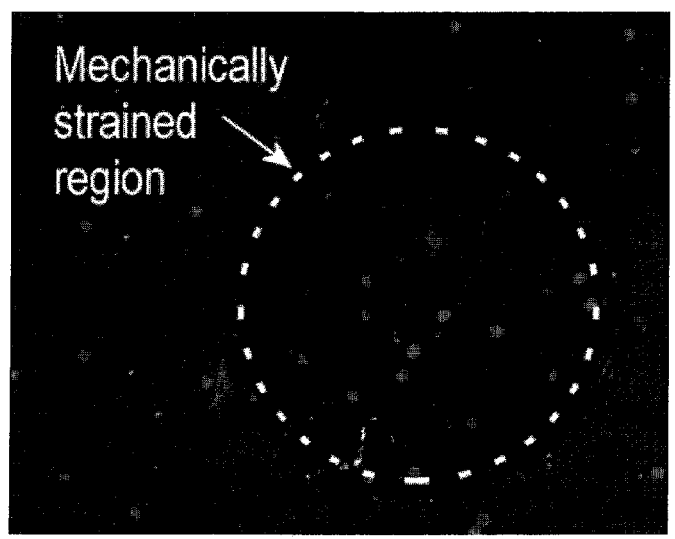
FIG. 20: Fluorescently stained image where Blue=Hoechst nuclear stain, and Red=BrdU stain for proliferating cells.
Figure 21:
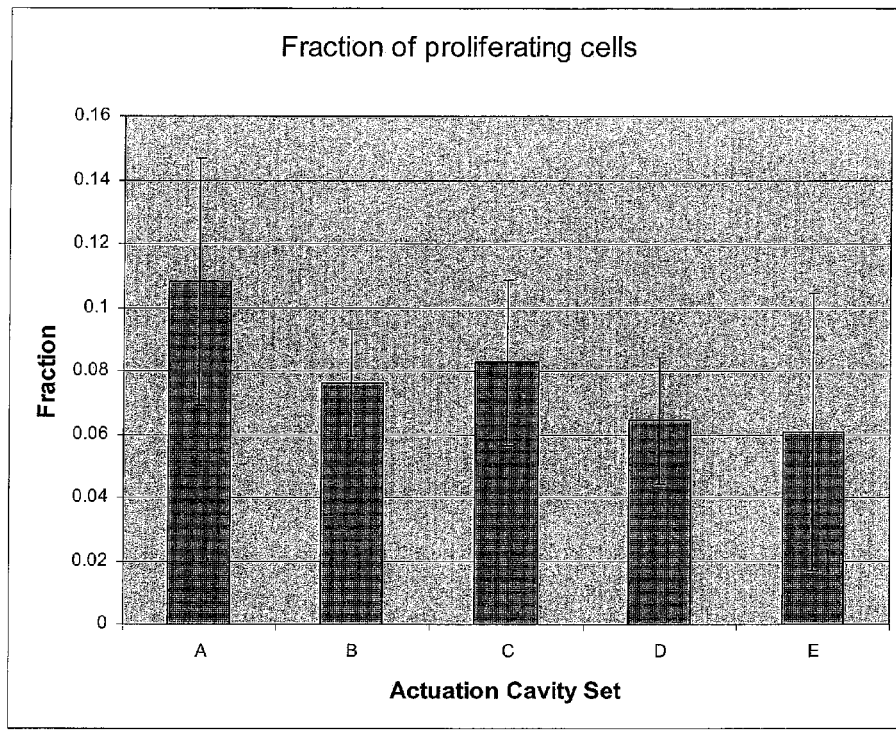
FIG. 21: Graph presenting results for the fraction of proliferating cells across mechanically active culture regions of the array.

The specific application of the particular experimental setup constructed is to provide uniform substrate strains as mechanical stimuli to determine the effects on biological cells grown on the culture membrane surface. As in the first embodiment of this invention, a PDMS well is used to hold cell culture media, to control the chemical stimuli seen by the cells, and to deposit ECM proteins prior to seeding the adherent cells. Also as in the first embodiment, standard techniques can also be used to pattern ECM protein type and concentration on individual units of the array. For a demonstration experiment, a mesenchymal stem cell line (C3H10T1/2) was seeded onto a polyurethane membrane, and subjected to cyclic 1 Hz strains ranging from 0 to 8% in 2% increments. The BrdU stain for proliferating cells was then used to determine the fraction of total cells that were proliferating, for each of the mechanically active regions (sample image shown in FIG. 20). Obtaining fluorescent images can require purging the oil lubrication channels if the oil autofluoresces at a specific excitation wavelength. This can be done with a soap and water solution. The results, shown in FIG. 21, demonstrate the practicality of using fluorescent analysis techniques to obtain data from cells cultured on the apparatus of the present invention.

Figure 22:
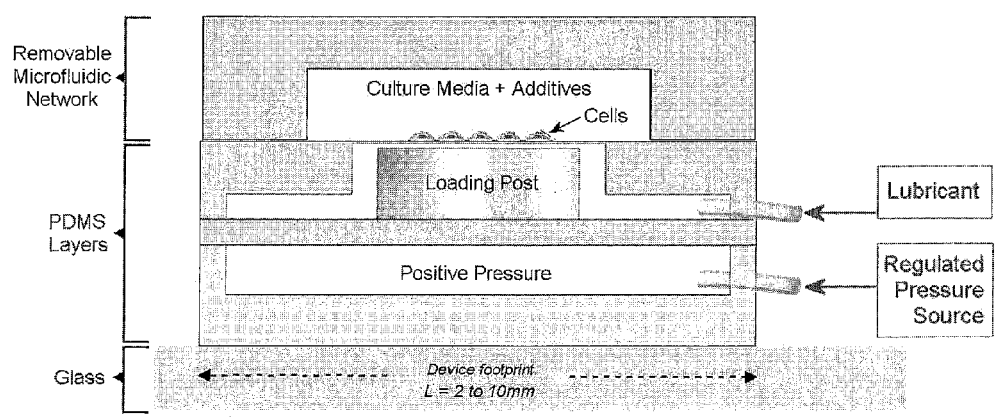
FIG. 22: Schematic illustrating the incorporation of microfluidic channels to deliver and control available chemical factors.

Although the apparatus of the present invention has been used for particular applications, the description of such is not intended to limit the scope of this invention. Theoretically, any culture membrane material that can be processed into a thin film can be used on the device. Any adherent cell type can be used, and because of the 1536-well plate format, currently available robotic dispensing is capable of controlling the chemical environment for individual units within the array. Furthermore, a microfluidic network can be incorporated (as in FIG. 22) to deliver precise quantities and combinations of chemicals to individual cell locations. Provided the chemicals are in liquid form, they can be distributed to each individual bioreactor. Examples of such chemical stimulation can include but are not limited to growth factors, hormones, cytokines, dissolved gases, and bioactive molecules. With this configuration, the bioreactor array can combinatorially probe cellular response to various mechanical strains, chemical cues, and extra-cellular matrix compositions. Controlling the flow rate of chemicals in the microfluidic channel also allows control over shear stresses exerted on the cells. Variations in shape of the loading post can create different strain fields in the culture membrane.

With reference to FIGS. 22 through 26 in a third embodiment, the present invention discloses a modification to the structure of the device 310, which allows compressive strains to be applied to a three-dimensional construct. This embodiment makes use of the lower portion of the above described embodiments—the culture membrane is removed entirely and the supporting structure for the culture membrane can optionally be removed. Three-dimensional constructs can then be fabricated with standard materials, including but not limited to natural or synthetic hydrogels, porous polymeric scaffolds, other tissue engineering scaffolds, biomaterials for cell encapsulation, native tissue or a custom-designed material. These constructs can be patterned and seeded with cells, using standard techniques (such as in Liu & Bhatia: "Three-dimensional Photopatterning of Hydrogels containing Living Cells", *Biomedical Microdevices*, 4, p 257, 2004).

Figure 23A:
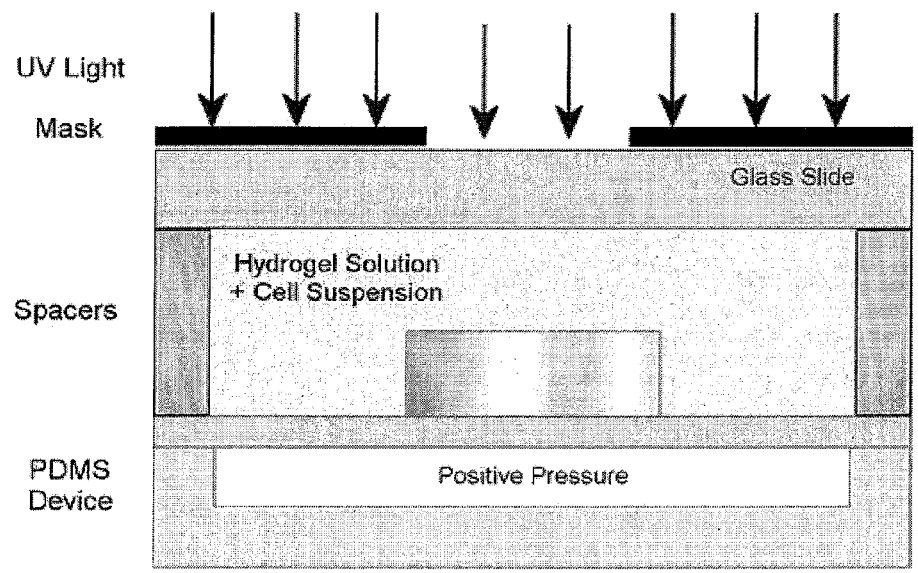
FIG. 23A, B: illustrates the procedure by which hydrogels can be micropatterned onto the device, creating an array of three dimensional constructs.
Figure 23B:
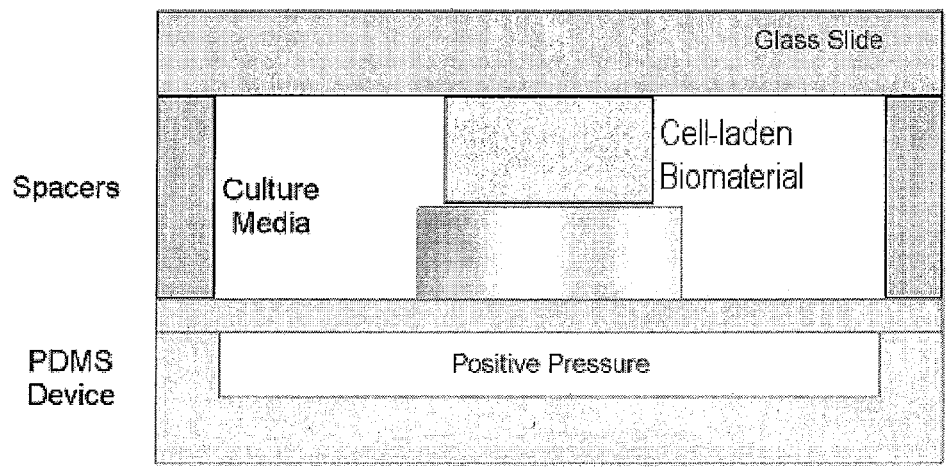
Figure 24A:
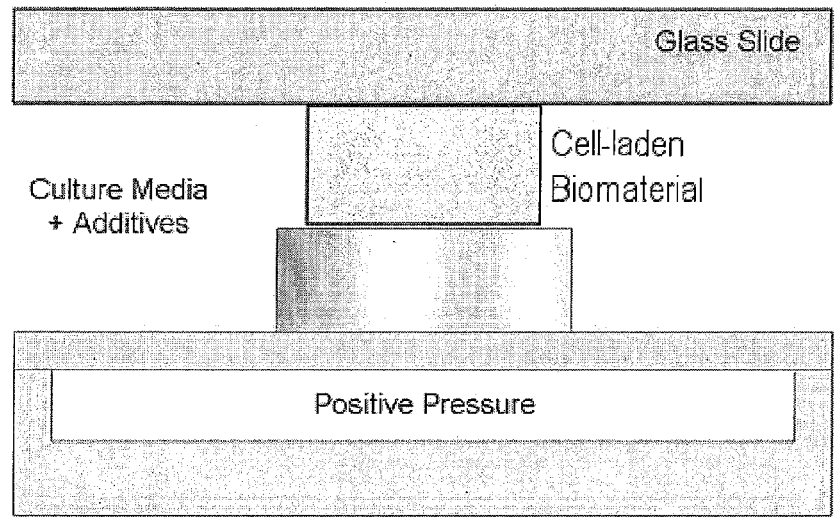
FIG. 24A, B: Schematic illustrating compressive loading of the constructs.
Figure 24B:
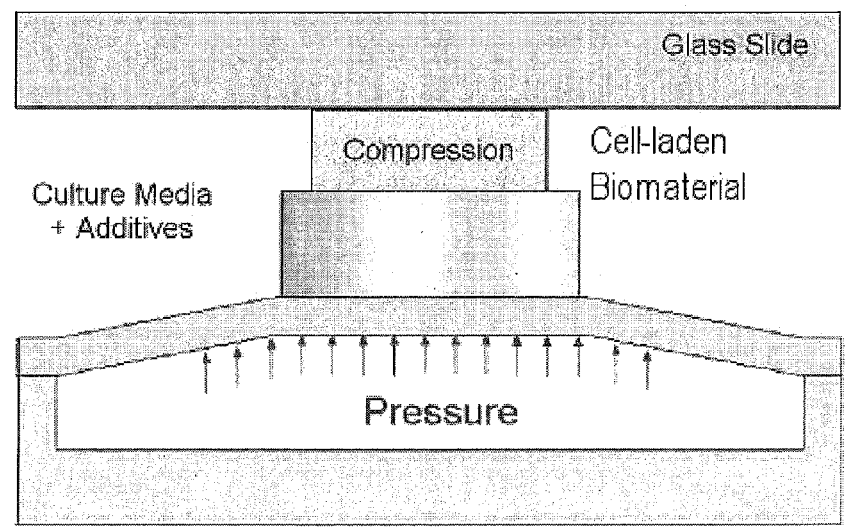
Figure 25:
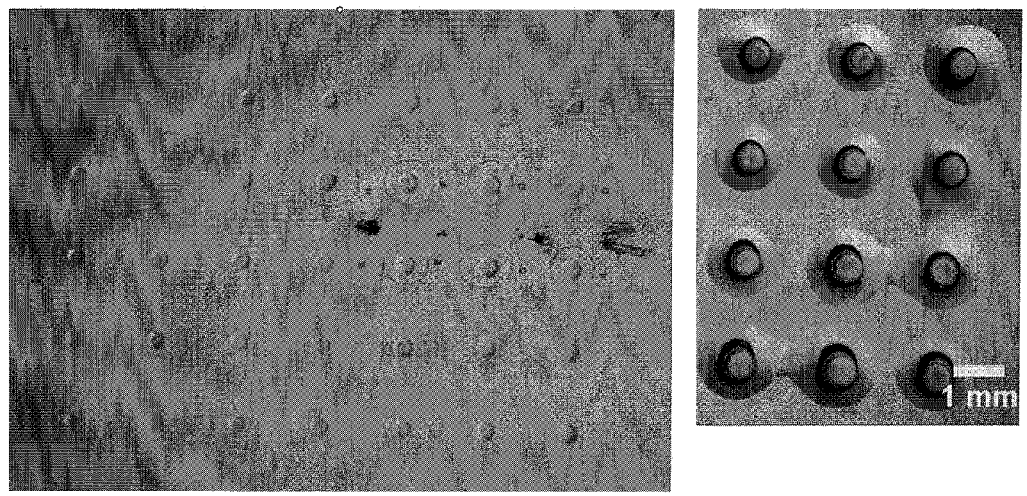
FIG. 25: Image demonstrating micropatterning of polyethylene glycol into an array of hydrogel cylinders.

FIGS. 23A-B illustrate the process by which a patterned hydrogel is photopolymerized atop the loading posts: a cell suspension and prepolymer mixture is flushed between the loading posts and a chemically functionalized glass slide. A mask is then aligned and placed atop the glass slide. UV light is then used to photopolymerize the array over the loading posts. FIG. 24 demonstrates compressive loading of the structure. Compressive loading is achieved using the same mechanism as in the previous embodiment: a pressure-actuated loading post atop an actuation cavity of varying dimensions. The loading posts squeeze the constructs against a holding means, which in this case comprises the functionalized glass slide.

This embodiment of the system can be used to study both adherent and non-adherent cell types. Non-adherent cell types would necessitate the use of an encapsulating polymer as the construct. Obtaining this setup is achievable by a number of methods—an alternative method is provided here: A cell suspension in pre-polymer solution can be prepared and patterned onto a glass substrate. The patterned constructs are then aligned with the array and spaced by means of a gasket. The setup is then mounted in a light clamp with appropriately flexible spacers. A positive pressure applied to the actuation cavity will bow the post upwards, compressing the construct (FIG. 24). Cycling the pressure will result in a dynamic, high-throughput compressive bioreactor array.

Figure 26:
FIG. 26: Cross-sectional view of the hydrogel cylinders fabricated.

To demonstrate the practicality of this approach, an array of cells encapsulated within photopolymerizable polyethylene-glycol (PEG) constructs are photopatterned on a chemically functionalized glass slide using a standard masking technique: The unpolymerized solution is then washed away, and the results, shown in FIG. 25 demonstrate the formation of large arrays of micropatterned cylinders. FIG. 26 illustrates a side view of one of the constructs. These arrays are then aligned with the device and clamped into place using a suitable supporting structure, for dynamic mechanical compressive stimulation.

The following numbers are reasonable estimates. The strain ranges for compressive testing are estimated to range between 0 and 80%—the upper end is limited by the porosity and stiffness of the construct, and the lower limit would depend on the size of the desired construct. Tensile testing can be expected to generate strains between 0 and 200%, based on finite element results for the distention of the loading post, and the minimum size of a desirable construct.

Figure 27:
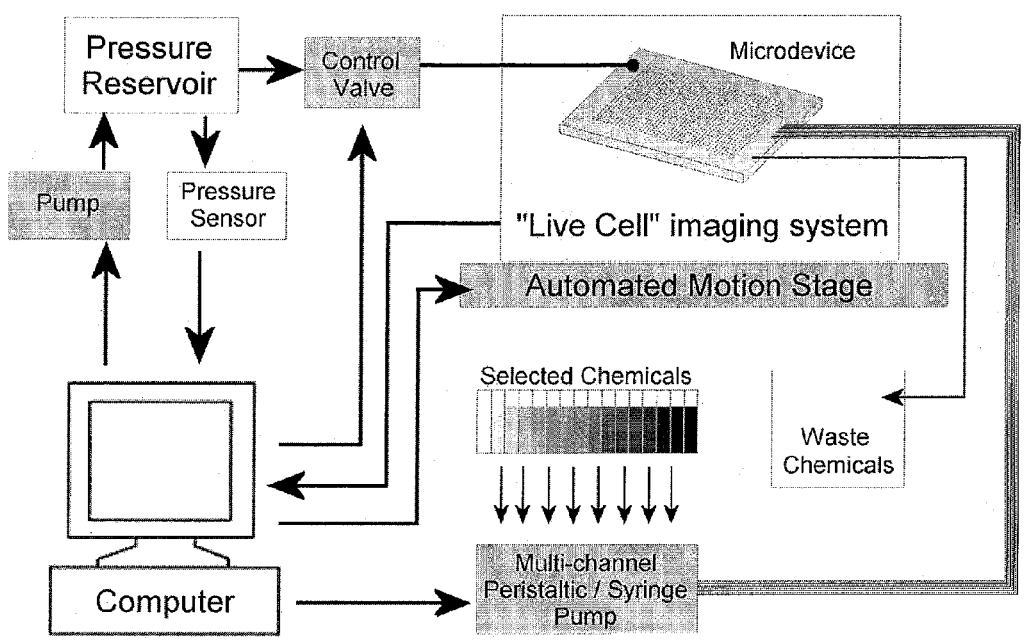
FIG. 27: Schematic of peripheral setups for each embodiment of the invention.

An idealized peripheral setup and integrated system for each of the embodiments described above is outlined in FIG. 27, which includes a computer controlled pump with a pressure sensor and valve to form a closed-loop control system for accurately applying dynamic pressures to the reactor array. The computer also controls chemical feed rates through a multichannel peristaltic or syringe pump, which provide nutrients to the cells, and can also be used to apply shear forces to each cell. The required control algorithms are simple and readily available in the public domain. The entire array is mounted in a 'live cell' imaging chamber, on an automated motion stage. The live-cell imaging system allows the cells to survive under a microscope for an extended period of time, and the motion stage will allow the microscope to take pictures of each unit at various time intervals. All this data can then be time-stamped and catalogued, and saved on the computer for subsequent automated or manual analysis.

We claim:

1. An apparatus for applying mechanical forces of varying magnitudes to a material characterized in that the apparatus comprises:
    (a) an array defining a surface and including a plurality of actuation devices disposed thereon, each actuation device including a cavity having an opening to the surface, the cavity having a structural configuration, at least one of the actuation devices in the array including a variation in the structural configuration;

(b) a flexible membrane fixed to the surface and covering said openings of the plurality of actuation devices in the array, each opening being covered by an area of the flexible membrane unsupported by the surface of the at least one array, said membrane having an upper surface that permits attachment of the material thereto, and (c) a network of channels connecting each cavity in the array to a single source of pressure or vacuum said channels being arranged to deliver a relatively equal amount of pressure or vacuum to the cavities, the unsupported areas of the flexible membrane covering the openings capable of being displaced upwardly relative to the surface upon delivery of pressure or downwardly relative to the surface upon the delivery of vacuum to the plurality of actuation devices, said displacement of the unsupported area of the flexible membrane being commensurate with the structural configuration of each of the plurality of actuation devices in the array and for applying mechanical force to the flexible membrane, whereby a single input of pressure or vacuum is translated into a range of mechanical forces of varying magnitudes being generated simultaneously across the plurality of actuation devices in the array.

2. The apparatus of claim 1 characterised in that the apparatus includes two or more arrays and the material comprises a biological material, the flexible membrane in each of the two or more arrays being patterned with different physiological compounds.

3. The apparatus of claim 1 characterised in that the variation of the structural configuration of the actuation device consists of variation of the lateral geometry of the cavity.

4. The apparatus of claim 1 characterised in that the actuation cavity includes a cavity wall having a thickness and wherein the variation of the structural configuration consists of a variation in the thickness of the cavity wall that affects the size of the unsupported area of the membrane covering the openings.

5. The apparatus of claim 1 characterised in that the flexible membrane covering the plurality of actuation devices are sufficiently thin so as to prevent bending stresses that result in non-uniform strain profiles.

6. The apparatus of claim 1 characterised in that the apparatus further comprises one or more wells wherein each well includes at least one of the one or more arrays.

7. The apparatus of claim 6 characterised in that the one or more wells are capable of containing a fluid thereby exposing the material to a chemical stimulus from said fluid.

8. The apparatus according to claim 1 characterised in that the apparatus is configured for an inverted microscope.

9. The apparatus according to claim 1 characterized in that said array is a high-density array of microscale actuation devices.

10. A method of high-throughput screening responses of a material to mechanical forces of varying magnitudes, characterised in that the method comprises:

(a) providing the apparatus of claim 1;
(b) delivering pressure or vacuum to the apparatus; and
(d) measuring the effect of said mechanical forces on the material.

11. An apparatus for applying mechanical forces of varying magnitudes to a material comprising:

(a) an array defining a surface and including a plurality of actuation devices disposed thereon, each actuation device including: (i) a base including a base cavity having a first opening and a structural configuration, at least one of the actuation devices including a variation in the structural configuration, (ii) a flexible actuation membrane fixed to the base and covering said first opening, each first opening being covered by an area of the actuation membrane unsupported by the base, said actuation membrane having an upper surface; (iii) an upper structure resting on said base, the upper structure including an upper cavity having a second opening that opens on the surface of the array, and (iv) a moving member extending from the upper surface of the unsupported areas of the actuation membrane into the upper cavity of the upper structure towards the second opening;

(b) a substrate membrane fixed to the surface of the array and covering said second openings, each second opening being covered by an area of the substrate membrane unsupported by the surface, said substrate membrane having an upper surface that permits attachment of the material thereto; and (c) a network of channels connecting each base cavity in the array to a single source of pressure or vacuum said channels being arranged to deliver a relatively equal amount of pressure or vacuum to the base cavities, the unsupported areas of the flexible actuation membrane covering the first openings capable of being displaced upwardly relative to the base upon delivery of pressure or downwardly relative to the base upon the delivery of vacuum to the plurality of actuation devices, said displacement of the flexible actuation membrane being commensurate with the variation in the structural configuration of each of the plurality of actuation devices in the at least one array, and said moving member capable of being moved upwardly towards the substrate membrane upon the upward displacement of the actuation membrane thereby displacing the substrate membrane upon delivery of pressure to the actuation devices, and to move downwardly away from the substrate membrane upon delivery of vacuum to the actuation devices, said displacement of the substrate membrane being commensurate with the structural configuration of each of the actuation devices and for applying mechanical force to the substrate membrane, whereby a single input of pressure or vacuum is translated into a range of mechanical forces of varying magnitudes being applied simultaneously across the plurality of actuation devices; and (d) a lubrication network of channels connecting each said upper cavities to a source of lubricant, said lubrication network operable to flush lubricant between the moving member and the substrate membrane.

12. The apparatus of claim 11 characterised in that the apparatus includes two or more arrays and the material comprises a biological material, the substrate membrane in each of the two or more arrays being patterned with different physiological compounds.

13. The apparatus of claim 11 characterised in that the variation of the structural configuration consists of variation of the lateral geometry of the actuation devices.

14. The apparatus of claim 11 characterised in that the actuation cavity includes a cavity wall having a thickness and wherein the variation of the structural configuration of the actuation devices consists of a variation in the thickness of the cavity wall that affects the size of the unsupported area of the membrane covering the openings.

15. The apparatus of claim 11 characterised in that the upper structure of at least one but not all of the actuation devices further includes structural means that limit the displacement of the actuation membrane.

16. The apparatus of claim 11 characterised in that the moving member includes structural means operable to reduce friction between the moving member and the substrate membrane.

17. The apparatus of claim 11 characterised in that the pressure actuated moving member is operable to produce a uniform strain field on the material.

18. The apparatus of claim 11 characterised in that the apparatus further comprises a micro fluidic network of channels for the delivery of a fluid to the upper structure, said delivery of fluid being capable of inducing shear stress on the material.

19. The apparatus of claim 11 characterised in that the apparatus further comprises a microfluidic network of channels for the delivery of a fluid to the upper structure said fluid being capable of inducing a chemical stimulus on the material.

20. The apparatus of claim 11 characterized in that the one or more arrays are disposed within wells configured for containing a fluid capable of inducing a chemical stimulus on the material.

21. A method of high-throughput screening responses of a material to mechanical forces of varying magnitudes, characterised in that the method comprises:
 (a) providing the apparatus of claim 11;
 (b) delivering pressure or vacuum to the apparatus; and
 (d) measuring the effect of said mechanical forces on the material.

22. An apparatus for applying mechanical forces of varying magnitudes to a material characterized in that the apparatus comprises:
 (a) an array defining a surface and including a plurality of actuation devices disposed thereon, each actuation device including a cavity having an opening to the surface, the cavity having a structural configuration, at least one actuation device including a variation in the structural configuration;
 (b) a flexible membrane fixed to the surface of the array and covering said openings of the plurality of actuation devices, each opening being covered by an area of the flexible membrane unsupported by the surface of the at least one array, said membrane having an upper surface;
 (c) a network of channels connecting each cavity in the array to a single source of pressure or vacuum said channels being arranged to deliver a relatively equal amount of pressure or vacuum to the cavities, the unsupported areas of the flexible membrane covering the openings capable of being displaced upwardly relative to the surface upon delivery of pressure and of being displaced downwardly relative to the surface upon delivery of vacuum to the plurality of actuation devices, said displacement of the unsupported flexible membrane being commensurate with the structural configuration of each of the plurality of actuation devices;
 (d) a moving member extending from the upper surface of each of the unsupported areas of the membrane, each moving member in the array having a top that permits attachment of the material thereto; and
 (e) a holding structure placed above the top of the moving member, said moving member capable of being moved upwardly towards the holding structure upon the upward displacement of the unsupported areas of the flexible membrane thereby compressing the material attached to the top against the holding structure, and capable of being moved downwardly away from the holding structure upon the downward displacement of the unsupported areas of the flexible membrane, said compression being commensurate with the structural configuration of the each of the actuation devices and for applying mechanical forces to the material, whereby a single input of pressure or vacuum is translated into a range of mechanical forces of varying magnitudes being applied simultaneously to the material.

23. The apparatus of claim 22 characterised in that the apparatus includes two or more arrays and the material comprises a biological material, the flexible membrane in each of the two or more arrays being patterned with different physiological compounds.

24. The apparatus of claim 22 characterised in that the variation of the structural configuration consists of variation of the lateral geometry of the cavity.

25. The apparatus of claim 22 characterised in that the cavity includes a cavity wall having a thickness and the variation of the structural configuration consists of a variation in the thickness of the cavity wall that affects the size of the unsupported area of the membrane covering the openings.

26. A method of high-throughput screening responses of a material to mechanical forces of varying magnitudes, characterised in that the method comprises:
 (a) providing the apparatus of claim 22;
 (b) delivering pressure or vacuum to the apparatus; and
 (d) measuring the effect of said mechanical forces on the material.

* * * * *